United States Patent
McWethy et al.

(10) Patent No.: US 7,004,929 B2
(45) Date of Patent: Feb. 28, 2006

(54) SAFETY PRE-FILLED CARTRIDGE INJECTOR

(75) Inventors: Robert T. McWethy, Ventura, CA (US); Bernardo Challiol, Ventura, CA (US); Joseph Kovalski, Ventura, CA (US); John Barker, Ventura, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 320 days.

(21) Appl. No.: 10/166,305

(22) Filed: Jun. 10, 2002

(65) Prior Publication Data

US 2003/0229314 A1 Dec. 11, 2003

Related U.S. Application Data

(63) Continuation of application No. PCT/US02/09614, filed on Mar. 29, 2002.

(51) Int. Cl.
*A61M 5/00* (2006.01)

(52) U.S. Cl. .......................... 604/198; 604/110
(58) Field of Classification Search ............... 604/198, 604/110, 192, 195, 228, 232, 263
See application file for complete search history.

(56) References Cited

U.S. PATENT DOCUMENTS

| | | |
|---|---|---|
| 4,585,445 A | 4/1986 | Hadtke |
| 4,655,751 A | 4/1987 | Harbaugh |
| 4,675,005 A | 6/1987 | DeLuccia |
| 4,723,943 A | 2/1988 | Spencer |
| 4,731,068 A | 3/1988 | Hesse |
| 4,737,144 A | 4/1988 | Choksi |
| 4,738,663 A | 4/1988 | Bogan |
| 4,744,790 A | 5/1988 | Jankowski et al. |
| 4,744,791 A | 5/1988 | Egolf |
| 4,767,413 A | 8/1988 | Haber et al. |
| 4,804,372 A | 2/1989 | Laico et al. |
| 4,820,275 A | 4/1989 | Haber et al. |
| 4,826,489 A | 5/1989 | Haber et al. |
| 4,834,717 A | 5/1989 | Haber et al. |
| 4,919,657 A | 4/1990 | Haber et al. |
| 4,931,040 A | 6/1990 | Haber et al. |
| 4,935,014 A | 6/1990 | Haber |
| 4,946,441 A | 8/1990 | Laderoute |
| 4,988,339 A | 1/1991 | Vadher |
| 5,067,945 A | 11/1991 | Ryan et al. |
| 5,078,698 A | 1/1992 | Stiehl et al. |
| 5,098,382 A | 3/1992 | Haber et al. |
| 5,167,632 A | 12/1992 | Eid et al. |
| 5,167,641 A | 12/1992 | Schmitz |
| 5,201,708 A | 4/1993 | Martin |
| 5,269,766 A | 12/1993 | Haber et al. |

(Continued)

*Primary Examiner*—Sharon Kennedy
(74) *Attorney, Agent, or Firm*—Stephen H. Eland; Dann, Dorfman, Herrell and Skillman

(57) ABSTRACT

A device is provided for injecting fluid from a pre-filled cartridge. The device includes a needle and a hollow barrel that holds a pre-filled cartridge. A needle retainer releasably retains the needle in an extended position so the needle can be inserted into a patient. A plunger in the rear of the barrel cooperates with the cartridge to expel fluid from the cartridge during an injection. After an injection, the needle is automatically retracted into the barrel when pressure is released from the plunger. A locking mechanism locks the contaminated needle and cartridge in the barrel after needle retraction. After use, the device may be safely disposed of in a sharps container.

24 Claims, 15 Drawing Sheets

U.S. PATENT DOCUMENTS

| | | |
|---|---|---|
| 5,306,258 A | 4/1994 | de la Fuente |
| 5,336,200 A | 8/1994 | Streck et al. |
| 5,346,480 A | 9/1994 | Hess et al. |
| 5,350,367 A | 9/1994 | Stiehl et al. |
| 5,358,491 A | 10/1994 | Johnson et al. |
| 5,360,408 A | 11/1994 | Vaillancourt |
| 5,368,568 A | 11/1994 | Pitts et al. |
| 5,405,326 A | 4/1995 | Haber et al. |
| 5,429,611 A | 7/1995 | Rait |
| 5,445,620 A * | 8/1995 | Haber et al. ............... 604/232 |
| 5,531,706 A * | 7/1996 | de la Fuente ............... 604/198 |
| 5,624,400 A * | 4/1997 | Firth et al. .................. 604/110 |
| 5,989,226 A * | 11/1999 | Hymanson .................. 604/198 |
| 5,997,512 A | 12/1999 | Shaw |
| 5,997,513 A | 12/1999 | Smith et al. |
| 6,033,387 A * | 3/2000 | Brunel ....................... 604/198 |
| 6,036,675 A | 3/2000 | Thorne et al. |
| 2001/0004970 A1 | 6/2001 | Hollister et al. |

\* cited by examiner

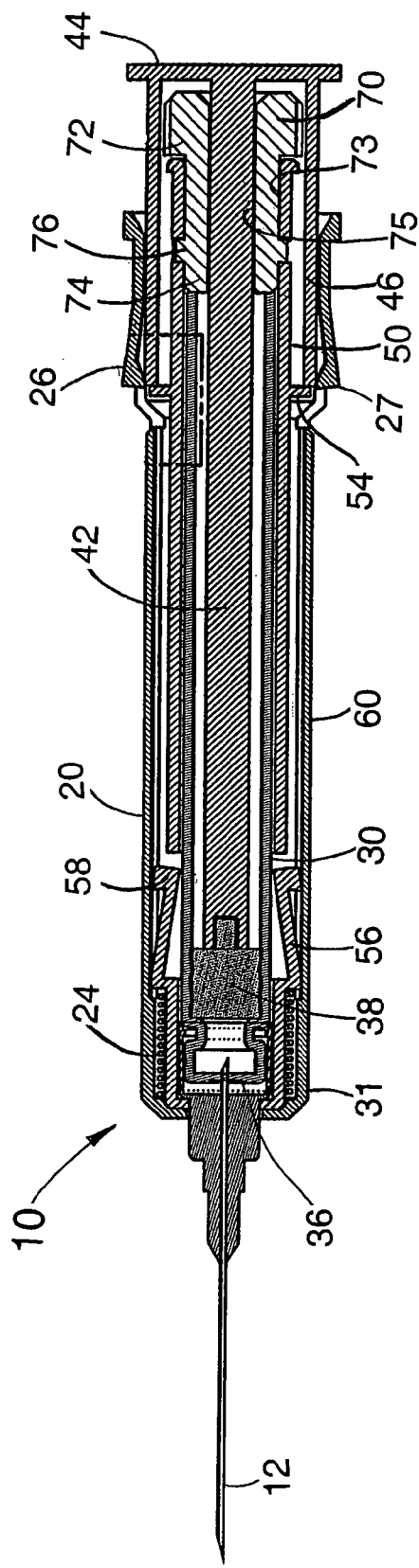

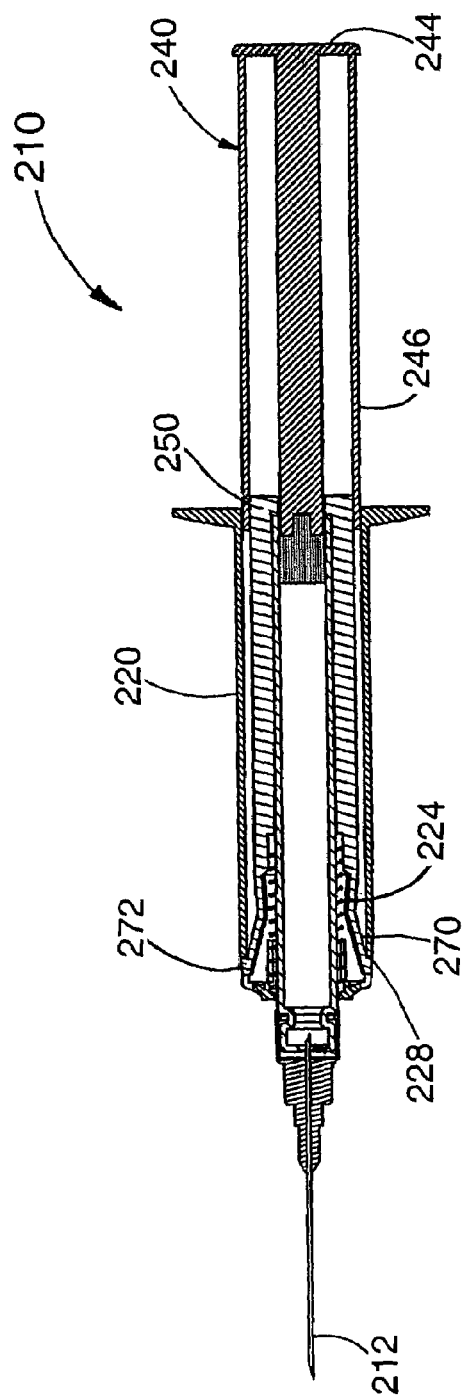
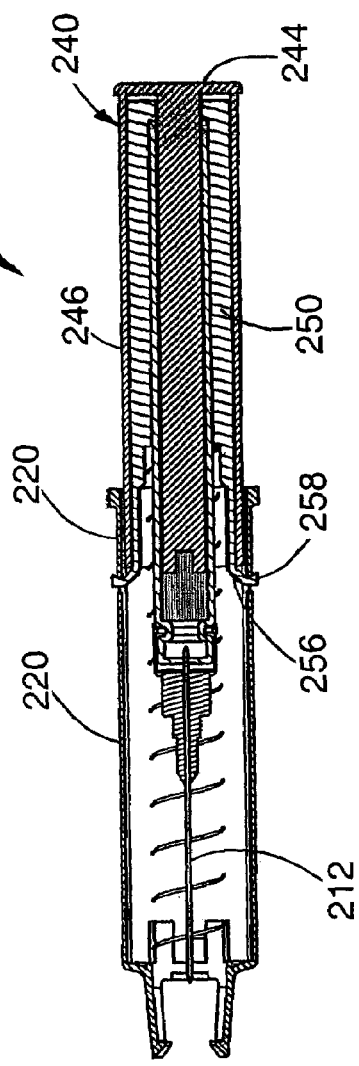
FIG. 13
FIG. 14

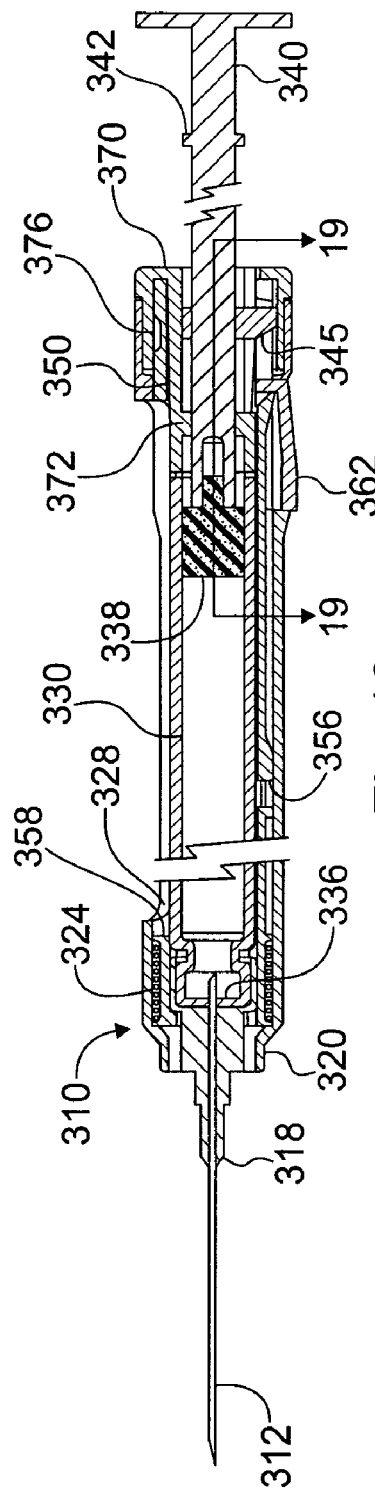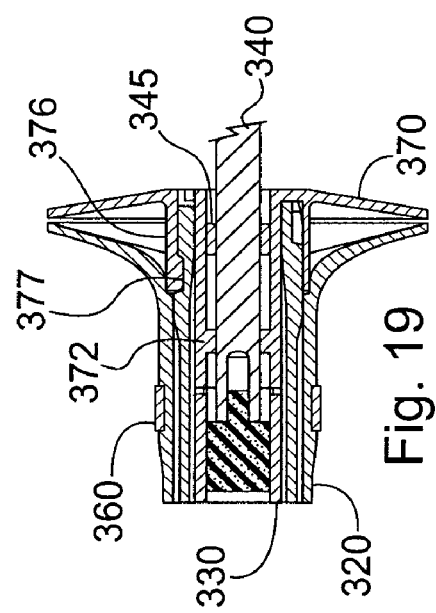
Fig. 18
Fig. 19

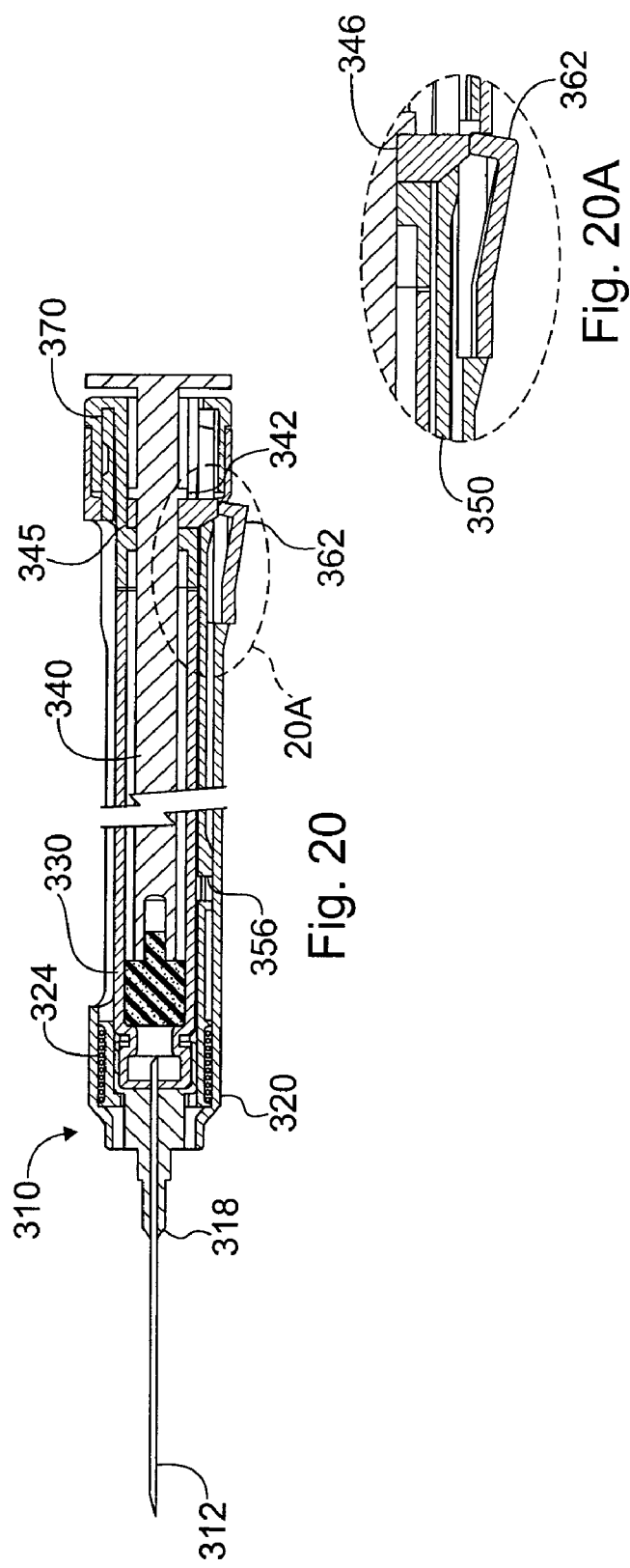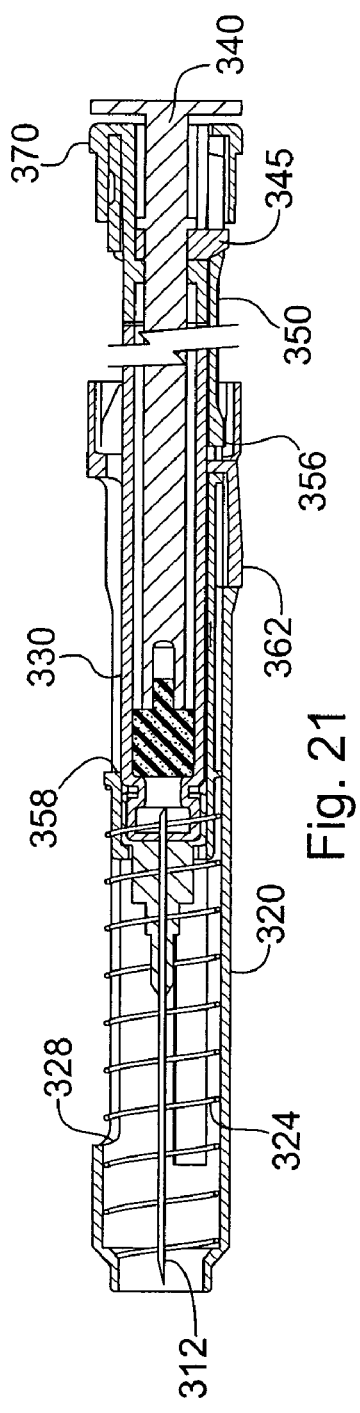

SAFETY PRE-FILLED CARTRIDGE INJECTOR

This application is a Continuation of International Patent Application No. PCT/US02/09614, filed on Mar. 29, 2002, which designates the United States and which is hereby incorporated herein by reference.

FIELD OF THE INVENTION

The present invention relates to devices for injecting a medication into a patient, and more specifically to needle devices that inject medicine from a pre-filled cartridge into a patient and automatically retract the needle after the injection so that the device can be safely discarded.

BACKGROUND

Medical professionals who use needle devices to treat patients face the risk of being pierced by contaminated needles. Widespread concern for various blood born pathogens, such as the AIDS virus, has led to advancements in needle devices. Many needle devices in the art now provide a mechanism for retracting the needle into an enclosure after the needle is removed from a patient. Once the needle is retracted in these devices, the medical professional can safely handle and dispose of the device. Over time, advancements have made retractable needle devices easier and safer to use. Some needle devices now have elements that prevent removal or reuse of contaminated needles once they are retracted into an enclosure.

Safety features have become desirable in a variety of needle devices, including devices that inject medication from pre-filled cartridges (i.e. "cartridge injectors"). In some cases, safety features have been retrofitted into prior art designs, or designed to accommodate existing parts, so as to retain existing components and minimize the need for new components. These changes have generally been unfavorable in terms of both design concerns and cost. In some cartridge injectors, the safety components are not compatible with commercially available medicine cartridges, and redesigned cartridges must be used in the device. In other cartridge injectors, the addition of safety features has added size and bulk to the device, making the device less desirable for use.

SUMMARY OF THE INVENTION

In light of the foregoing, the present invention provides a needle device that is compatible with standard pre-filled cartridges. The device allows medication to be injected from a pre-filled cartridge through a needle. The cartridge is housed in a hollow barrel, and a double-ended needle connects with the cartridge. The needle is operable between a projecting position in which the needle is exposed for use, and a retracted position in which the needle is shielded against inadvertent contact. The rear end of the barrel contains a plunger that engages the rear end of the cartridge. Medication is expelled from the cartridge by applying pressure on the plunger.

At the end of the injection stroke, the needle and cartridge are automatically retracted into the barrel by releasing pressure on the plunger. No positive action is required at the end of the injection stroke to retract the needle. During retraction, a cartridge holder conveys the needle through the barrel. A biasing element, such as a compressed spring, acts on the cartridge holder to move the cartridge holder, needle and cartridge rearwardly into the barrel. A locking mechanism substantially prevents the needle from being accessed once the needle is retracted.

DESCRIPTION OF THE DRAWINGS

The foregoing summary as well as the following description will be better understood when read in conjunction with the figures in which:

FIG. 5 is a cross-sectional view of the cartridge injector shown in FIG. 1 illustrating the device at the end of an injection;

FIG. 6 is a cross-sectional view of the cartridge injector shown in FIG. 1 illustrating the device after retraction of the needle;

FIG. 13 is a cross-sectional view of the device shown in FIG. 11, illustrating needle retaining arms in engagement with the front end of the barrel;

FIG. 14 is a cross-sectional view of the device shown in FIG. 11, illustrating the device after retraction of the needle;

FIG. 18 is a cross-sectional view of the device illustrated in FIG. 17, showing the device in a ready-for-use position;

FIG. 19 is a fragmentary cross-sectional view of the device illustrated in FIG. 18, taken along the line 19—19;

FIG. 20 is a cross-sectional view of the device illustrated in FIG. 17, showing the device at the end of an injection;

FIG. 20A is an enlarged fragmentary detail view of the portion of the device identified in FIG. 20; and FIG. 21 is a cross-sectional view of the device illustrated in FIG. 17, showing the device after retraction.

DETAILED DESCRIPTION OF THE PREFERRED EMBODIMENT

Figure 1:
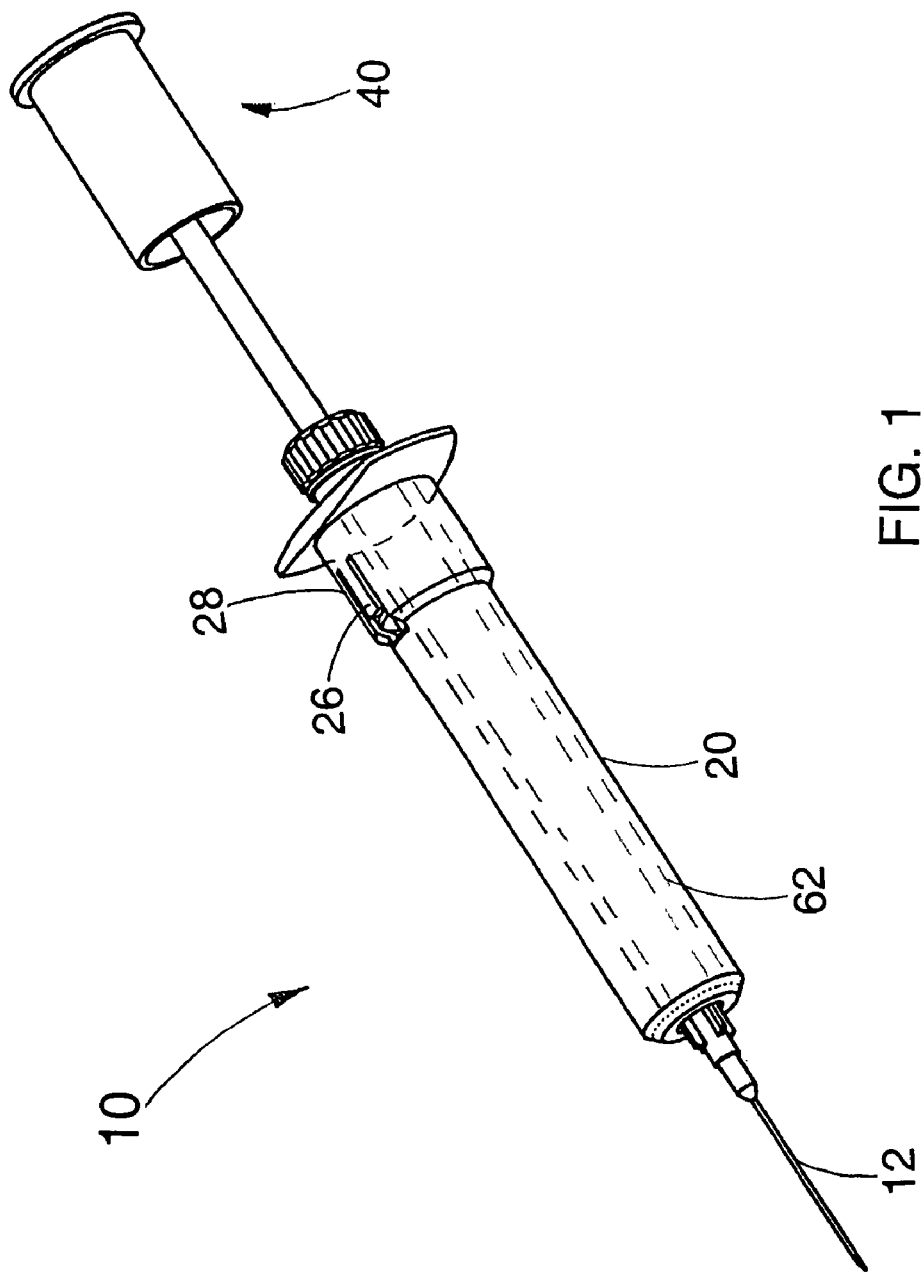
FIG. 1 is an perspective view of a safety cartridge injection device.

Referring to FIGS. 1–14 in general, and to FIGS. 1–6 specifically, a device 10 for injecting a medication from a pre-filled cartridge 30 is shown. The cartridge injector 10 includes a hollow cylindrical barrel 20, the pre-filled cartridge 30 disposed within the barrel, a needle 12 extending forwardly from the cartridge and a plunger 40 slidably disposed in the rearward end of the barrel. The plunger 40 is operable to expel medication from the cartridge 30 and through the needle 12 into a patient. After the plunger 40 has expelled substantially all the medication from the cartridge, the needle 12 is automatically retracted into the barrel 20 where it is shielded from inadvertent contact.

The needle 12 and cartridge 30 are maintained in axial alignment with barrel 20 by a cartridge holder 50 disposed between the cartridge and the inside wall of the barrel. A compression spring 24 circumscribes the forward end of cartridge holder 50 and is compressed against the interior of the barrel 30 at the barrel's forward end. The rearward end of spring 24 bears against the forward end of cartridge holder 50 to bias cartridge holder and needle 12 in the rearward direction. After the completion of an injection stroke, spring 24 expands to displace the cartridge holder 50, needle 12 and cartridge 30 rearwardly into the device. The barrel 20 and cartridge holder 50 are preferably formed of a transparent or translucent plastic material.

Figure 4:
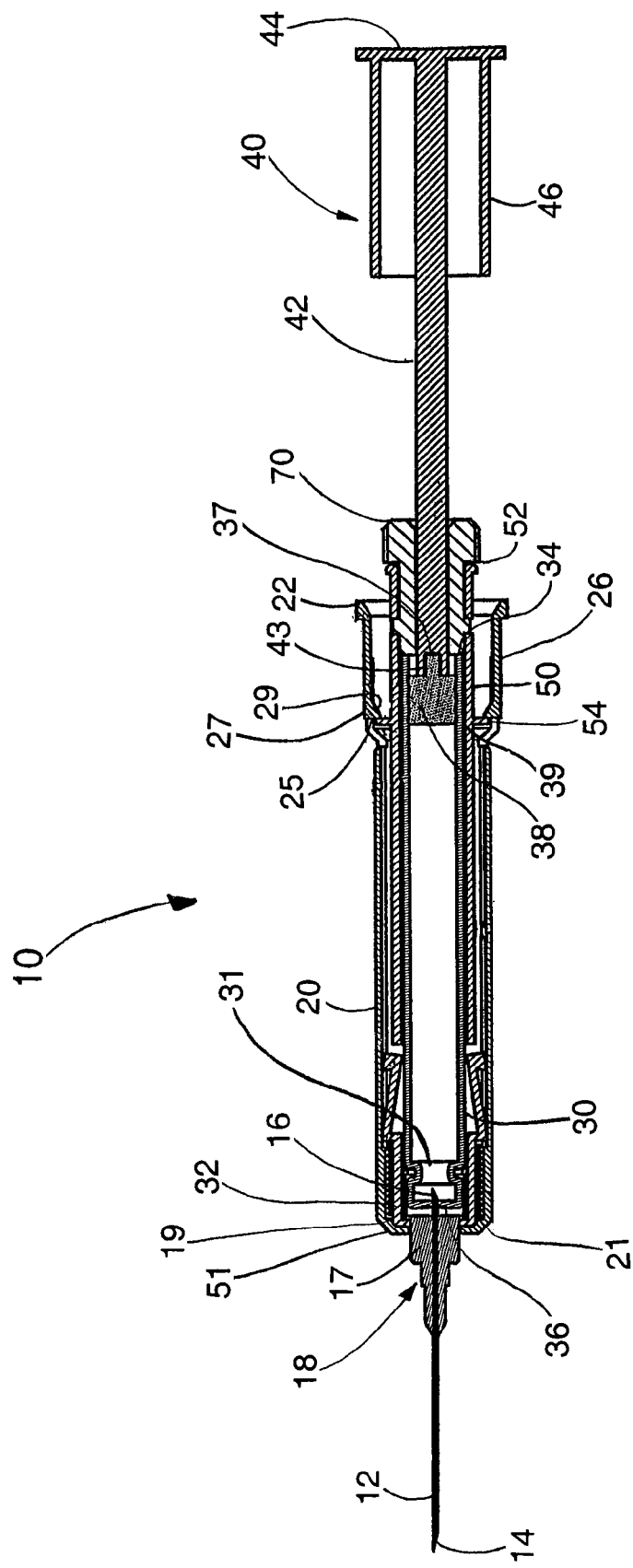
FIG. 4 is a cross-sectional view of the cartridge injector shown in FIG. 1 illustrating the device prepared for an injection.

The cartridge injector 10 is intended for use with a variety of commercially available needles and cartridges, or alternatively, commercially available assemblies that include an injection needle connected to a pre-filled cartridge. In FIG. 4, the device 10 is shown with a Carpuject cartridge-needle assembly manufactured by Abbot Laboratories, Inc.

Referring now to FIG. 4, device 10 will be described in greater detail. Needle 12 is a double-ended needle having a sharpened forward tip 14 and sharpened rearward tip 16. The needle is operable between an extended position, in which forward tip 14 extends forwardly from the forward end of barrel 20, and a retracted position, in which the forward tip is enclosed within the barrel. A needle hub 18 is disposed around needle 12 such that forward tip 14 extends forwardly from the forward end of the hub and rearward tip 16 extends rearwardly from the rearward end of the hub. A removable needle cover 13 (see FIG. 2) connects to needle hub 18 and covers the forward tip 14 of needle 12 prevent inadvertent needle sticks prior to use.

Cartridge 30 is generally cylindrical having a forward end 32 and open rearward end 34. The forward end 32 of cartridge 30 is enclosed by a pierceable septum 36 that provides a fluid tight seal at the forward end of the cartridge. A cylindrical plug 38 is slidably disposed in the open rearward end 34 of cartridge 30. The plug 38 frictionally and sealingly engage the interior of cartridge 30 to prevent fluid from leaking from the cartridge. Plug 38 may be molded in a biocompatible elastomer such as polyisoprene.

As present in many cartridges in the art, cartridge 30 has a reduced diameter neck 31 toward the forward end of the cartridge, as shown in FIG. 4. The reduced inside diameter of the neck 31 is less than the diameter of plug 38. As such, plug 38 is axially displaceable between the rearward end of the cartridge and the neck 31. In particular, plug 38 is forwardly displaceable until the forward end of plug 38 contacts the rear edge of neck 31.

Plunger 40 is operable to expel medication from the cartridge 30. Plunger 40 is preferably formed of molded plastic and comprises an elongated plunger rod 42 connected to a finger pad 44 at the rearward end of the rod. A cylindrical collar 46 extends forwardly from finger pad 44 and circumscribes plunger rod 42. Plunger rod 42 is configured to engage plug 38 in cartridge 30 such that the plug can be displaced in the cartridge when pressure is applied to the finger pad 44. Preferably, plunger rod 42 is releasably connected to the plug 38 so that the plunger can be detached from device 10 after use, if desired. As shown in FIG. 4, plug 38 has a reduced diameter threaded projection 37 that extends rearwardly from the rearward end of the plug. The forward end of plunger rod 42 has a shallow bore 43 having internal threads configured to cooperate with the threads on the threaded projection 37 of plug 38. Once the plunger rod 42 is screwed onto plug 38, plunger 40 is operable to axially displace the plug and expel medication from cartridge 30.

Figure 2:
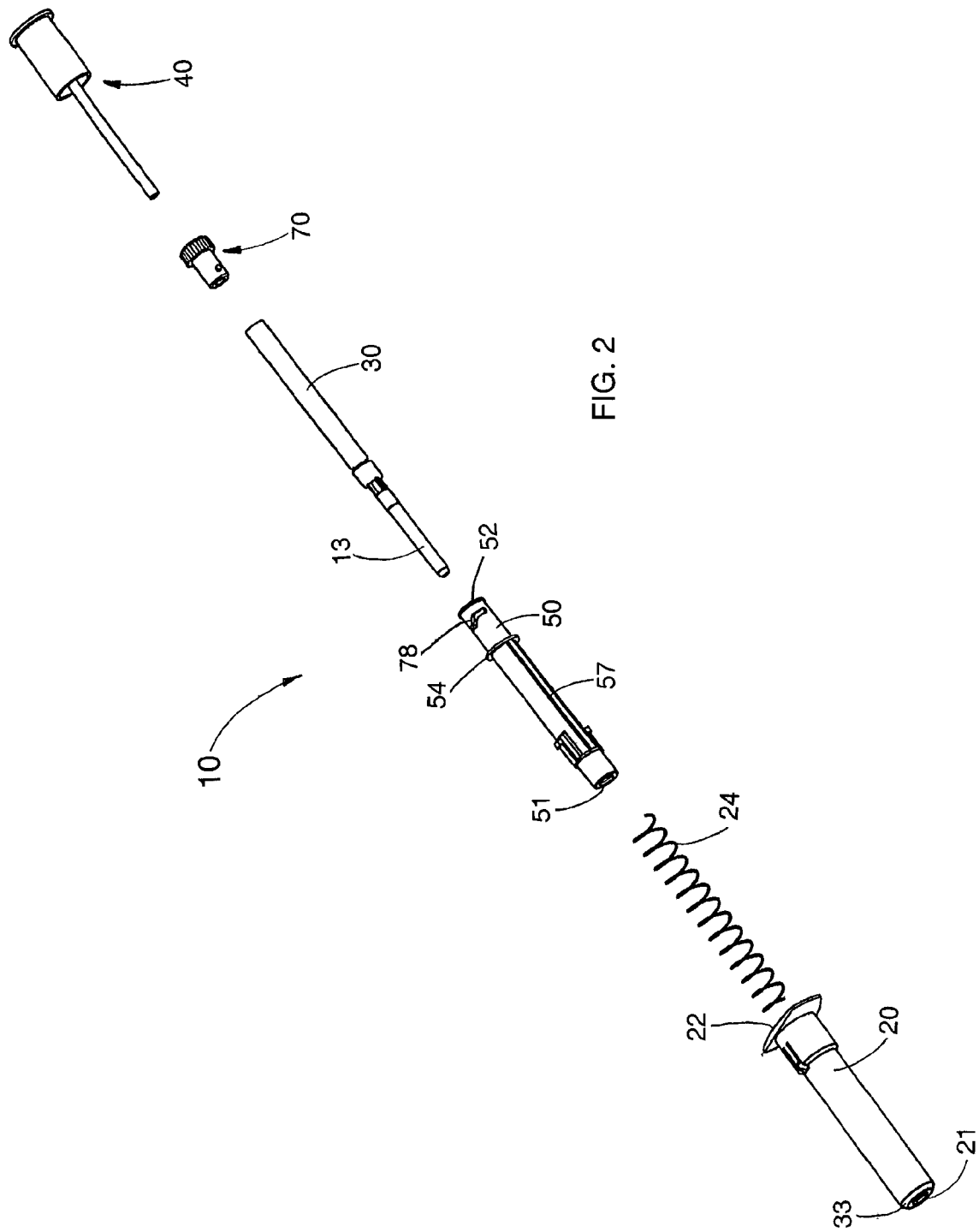
FIG. 2 is an exploded perspective view of the cartridge injector shown in FIG. 1.

Referring now to FIGS. 2 and 4, cartridge holder 50 is generally cylindrical and is preferably formed of molded plastic. Cartridge holder 50 has an open forward end 51 and open rearward end 52. Rearward end 52 is adapted to receive needle 12, needle hub 18 and cartridge 30. The outside diameter of cartridge 30 is preferably less than the inside diameter of cartridge holder 50 such that the cartridge slides easily into the cartridge holder during loading. As shown in FIG. 2, cartridge holder 50 has a pair of opposed ribs 57 that extend longitudinally along the exterior of the cartridge holder. In addition, cartridge holder 50 has a circumferential flange 54 that extends radially outwardly near the rearward end of the cartridge holder. Ribs 57 and flange 54 cooperate with the barrel during operation of the device, as discussed further below.

The barrel 20 is generally cylindrical and is formed of a transparent or translucent molded plastic. Barrel 20 has a forward end 21 and open rearward end 22. Forward end 21 has a circular aperture 33 adapted to receive needle 12 and needle hub 18 such that the needle and needle hub project forwardly from the barrel. Needle hub 18 has a base 17 and flange 19 extending radially outwardly at the rearward end of the base. The diameter of the flange is greater than the diameter of aperture 33 in the forward end of barrel 20 so that needle hub 18 is prevented from passing through the forward end of the barrel. Open rearward end 22 of barrel 20 is adapted to receive the cartridge holder within the needle 12, needle hub 18 and cartridge 30, such that the cartridge and needle can be loaded through the rearward end of the device 10.

Prior to use, the cartridge 30 is sealed so that medication does not leak out of the cartridge. In particular, cartridge 30 has a pierceable septum 36 that provides a fluid tight seal in the forward end of the cartridge. Generally, it is desirable to keep cartridge 30 sealed until the time of the injection to minimize loss of the medication through leakage. In light of this, the device 10 is configured so that cartridge 30 can be unsealed in the device immediately prior to an injection.

Figure 3:
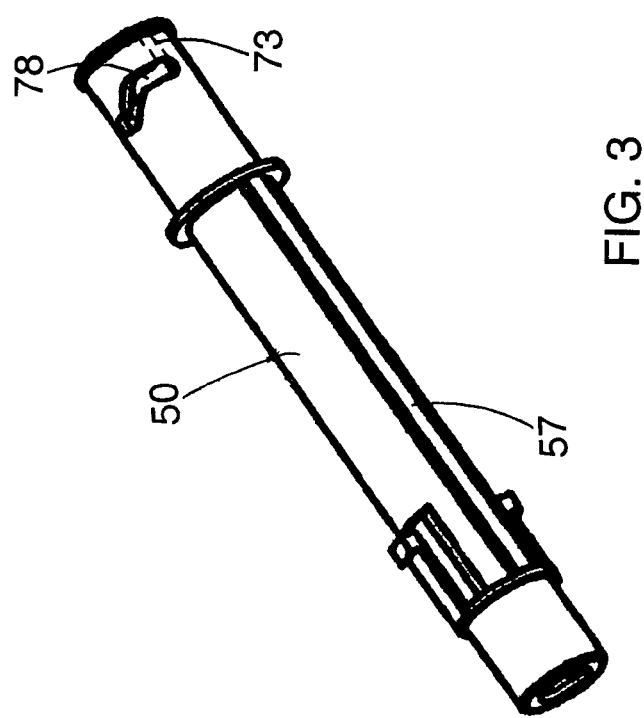
FIG. 3 is a perspective view of a cartridge holder component in the cartridge injector shown in FIG. 1.

Referring now to FIGS. 2-4, a plastic molded advancer dial 70 is disposed in the rearward end of cartridge holder 50. Advancer dial 70 is operable to impart an axial force on the cartridge sufficient to move the pierceable septum 36 into contact with needle 12 and pierce the septum. Advancer 70 comprises an enlarged diameter hub 72 molded to a reduced diameter shaft 74. In addition, advancer 70 has an interior bore 75 adapted to receive plunger rod 42 to allow the plunger rod to be connected to cartridge plug 38. Bore 75 is preferably coaxial with cartridge 30 and cartridge holder 50. In addition, the inside diameter of bore 75 is preferably larger than the diameter of plunger rod 42 to allow the rod to slide freely through advancer 70. A pair of opposed bosses 76 are disposed 180 degrees apart on the exterior of shaft 74 and extend radially outwardly from the shaft. Bosses 76 are configured to slidably engage a pair of opposed helical channels 78 that extend through the cartridge holder wall near the rearward end of the cartridge holder. A pair of opposed keyways 73 extend longitudinally in the interior wall of cartridge holder 50. One of the keyways is visually represented by dashed lines in FIG. 3. Keyways 73 connect the rearward end of the cartridge holder with the rearward portion of each channel 78. The keyways 73 are adapted to receive bosses 76 on advancer 70 and guide the bosses to the rearward portion of channels 78 as the advancer is inserted into the cartridge holder 50.

When bosses 76 are disposed in channels 78, the channel walls engage with the sides of the bosses to control the position of the advancer as it is rotated. Helical channels 78 extend toward the forward end of cartridge holder 50 from a point where the channels adjoin keyways 73, as shown in FIG. 3. As such, helical channels 78 are configured to guide the advancer forwardly into cartridge holder 50 as the advancer is rotated. The length of each channel 78 is relatively small, such that the advancer hub 72 only needs to be rotated through a small angle of rotation. Preferably, channels 78 are oriented such that the required angle of rotation of hub 72 is less than 90 degrees. In addition, channels 78 are preferably oriented so that advancer 70 moves forwardly when advancer hub 72 is rotated clockwise.

Advancer shaft 74 is longitudinally aligned with the rearward end of cartridge 30 when advancer 70 is inserted into cartridge holder 50. To permit insertion of advancer shaft 74 into cartridge holder 50, the axial length of the cartridge holder is greater than the axial length of cartridge 30, as shown in FIG. 4. The forward end of advancer shaft 74 is configured to abut the rear end of cartridge 30 as advancer 70 is partially rotated into the rear end of cartridge holder 50. Once advancer shaft 74 contacts the rear end of cartridge 30, continued rotation of advancer hub 72 forces the cartridge forwardly into contact with the rear tip 16 of needle 12 and the needle hub 14. The compressive force applied to cartridge 30 causes rear tip 16 of needle 12 to puncture the septum 36. The compressive force also pushes the forward edge of septum 36 into contact with the rear edge of needle hub 14 so as to provide a fluid tight seal around the pierced septum.

Once needle 12 and cartridge 30 are loaded into the device 10, the barrel 20 cooperates with the cartridge holder 50 to maintain the needle in the extended position against the bias of spring 24. As illustrated in FIGS. 1 and 2, a pair of resiliently flexible retainer arms 26 are formed by a pair of partial rectangular cut outs 28 in the barrel wall. Retainer arms 26 are preferably disposed along the barrel 180 degrees apart from one another and extend longitudinally along the barrel wall near the rearward end of the barrel. Each arm 26 has a fixed rearward end on the barrel wall and a free forward end, as shown in FIG. 4.

A retaining latch 27 on the free end of each retaining arm 26 protrudes inwardly into the interior of barrel 20. The latches 27 are configured to contact flange 54 on cartridge holder 50 to maintain the needle in the extended position. Each latch 27 has a substantially vertical forward face 25 and a tapered rearward face 29. Prior to retraction of the needle, retainer arms 26 are in an engaged position with cartridge holder 50, as shown in FIG. 4. In particular, retainer arms 26 are oriented generally parallel to the longitudinal axis of barrel 20. In the engaged position, latches 27 on arms 26 protrude radially inwardly into the interior of barrel 20 such that the forward face 25 of each latch confronts the rearward side of flange 54 on cartridge holder 50. The latches 27 engage the cartridge holder 50 to retain the cartridge holder in a forward position against the bias of spring 24, thereby maintaining needle 12 in the extended position relative to barrel 20. The arms 26 are radially deformable such that after use the arms are pushed radially outwardly to release the cartridge holder 50, as discussed further below.

Plunger 40 is slidably disposed in barrel 20 such that axial pressure on finger pad 44 axially advances plunger rod 42 toward the forward end of the barrel. Prior to an injection, finger pad 44 and plunger collar 46 are disposed outside the rearward end of barrel 20, as shown in FIGS. 1 and 4. During an injection stroke, collar 46 and plunger rod 42 advance forwardly into the barrel. More specifically, collar 46 is integrally connected with finger pad 44 and advances forwardly into the rearward end of barrel 20 as the axial pressure is applied to the finger pad.

As plunger 40 is advanced forwardly, the forward end of collar 46 advances toward the tapered rearward edge 29 of each latch 27. Rear edges 29 are tapered radially inwardly with respect to the barrel, converging toward the barrel axis as the latch extends toward the forward end of the barrel. As plunger collar 46 is displaced forwardly into contact with latches 27, the forward end of the plunger collar rides along rear edges 29 and displaces the retaining arms 26 radially outwardly. More specifically, as plunger collar 46 contacts the tapered rear edges 29 of latches 27, forces on the latches are directed radially outwardly by the orientation of tapered rear edges, causing the retaining arms 26 to deflect radially outwardly from the barrel.

As retaining arms 26 are deflected outwardly, latches 27 are gradually displaced from the engaged position to a released position, as illustrated in FIG. 5. In the released position, latches 27 are deflected outwardly from barrel 20, disengaging the flange 54 on cartridge holder 50. Plunger collar 46 is aligned longitudinally with flange 54 such that the forward edge of the collar contacts the rear edge of the flange as latches 27 are displaced out of engagement with the flange. As such, latches 27 no longer maintain cartridge holder 50 toward the forward end of barrel 20 against the bias of spring 24. Rather, cartridge holder 50 is maintained in the forward end of the barrel 20 against the bias of spring 24 by axial pressure applied on finger pad 44 and plunger collar 46. Upon removal of axial pressure on finger pad 44 and collar 46, the force exerted by spring 24 on cartridge holder 50 is no longer counteracted, allowing spring 24 to expand and displace the cartridge holder rearwardly into the barrel 20, as shown in FIG. 5.

When the forward end of plunger collar 46 is advanced toward the tapered rearward edges 29 of latches 27, plunger rod 42 advances plug 38 in cartridge 30 to expel medication from the cartridge. In particular, the forward edge of plug 38 advances toward the rearward edge of neck 31 to displace medication out of the forward end of cartridge 30. Preferably, the longitudinal distance between the forward end of plunger collar 46 and rearward edge of flange 54 is equal to the longitudinal distance between the forward edge of plug 38 and rearward edge of neck 31. In this way, the retaining arms 26 are not disengaged until substantially all of the medication is expelled from cartridge 30.

Preferably, a mechanism is provided to limit rearward displacement of the cartridge holder 50 during retraction such that the cartridge holder and needle 12 are not displaced out the rear end of barrel 20. In addition, it is desirable to prevent the needle from being deliberately removed from the barrel after it is retracted. Referring now to FIGS. 5 and 6, a pair of resiliently flexible lockout arms 56 are molded to cartridge holder 50 and extend radially outwardly from the forward end of the cartridge holder. Each lockout arm 56 has a lockout tab 58 extending radially outwardly at the rearward end of the arm. Prior to assembly of the device 10, lockout arms 56 extend parallel to the longitudinal axis of cartridge holder 50. To insert cartridge holder 50 into barrel 20, lockout arms 56 are deflected radially inwardly toward one another so that lockout tabs 58 can enter the rearward end of barrel. As a result, lockout arms 56 are biased radially outwardly in the barrel. A pair of lockout windows 23 disposed at the rearward end of barrel 20 are adapted to receive lockout tabs 58 as cartridge holder 50 is projected rearwardly during needle retraction. In particular, lockout windows 23 are positioned such that lockout tabs 58 align with the windows during retraction of the needle and snap outwardly into engagement with the windows. Lockout tabs 58 are configured to extend outwardly into the lockout windows such that the sides of the tabs contact the sides of the windows to prevent further axial displacement of cartridge holder 50 after retraction of needle 12.

To properly engage lockout windows 23, lockout tabs 58 are maintained in longitudinal alignment with the windows during operation of the device 10. A pair of grooves 60 extend longitudinally in barrel 20 in the interior of the barrel wall. The grooves 60 are adapted to receive lockout arms 56 and lockout tabs 58 on cartridge holder 50 during assembly of the device 10. Lockout arms 56 and lockout tabs 58 are slidably disposed in the grooves 60, and sidewalls in the grooves engage with the lockout arms and lockout tabs to prevent rotation of the cartridge holder in the barrel. Grooves 60 extend toward the rearward end of barrel 20 in alignment with lockout windows 23. As such, grooves 60 maintain the lockout tabs 58 in longitudinal alignment with the lockout windows 23.

Rotation of cartridge holder 50 is further limited by a pair of opposed ribs 57 that extend longitudinally along the exterior of the needle retainer, as shown in FIGS. 2 and 3. Opposed ribs 57 are oriented 90 degrees from the two lockout arms 56 and are slidably disposed in a pair of slots 62 in the interior wall of barrel 20. Slots 62, which are visually represented as dashed lines in FIG. 1, are oriented 90 degrees from the opposed grooves 60 and extend longitudinally along the interior wall of barrel 20. The sidewalls of slots 62 engage the sides of ribs 57 to prevent rotation of needle retainer 50 relative to the barrel. Lockout arms 56 and ribs 57 limit rotation of the cartridge holder 50 during use of the device 10. For example, lockout arms 56 and ribs 57 limit rotation of cartridge holder 50 when torque is transferred to the cartridge holder during rotation of the advancer 70 into the cartridge holder.

The spring 24 is operable to retract the needle to the retracted position, as stated earlier. Spring 24 is preferably formed of stainless steel. The stored energy in compressed spring 24 is sufficient to displace needle 12, needle hub 18, cartridge 30 and cartridge holder 50 rearwardly. In particular, compressed spring 24 has sufficient stored energy to overcome frictional resistance between cartridge holder 50 and the interior of barrel 20 and any frictional resistance between needle hub 18 and the forward end of the barrel. The device 10 may be manufactured and distributed with a cartridge 30 loaded in the barrel 20 and a plunger 40 connected to the cartridge. Alternatively, the device 10 can be distributed without a cartridge loaded in the barrel and with the plunger 40 detached from the cartridge.

Referring now to FIGS. 4–6, the device 10 is operated as follows. The device 10 is prepared for use by inserting a needle 12 with a needle cover 13 and pre-filled cartridge 30 through the rear end of barrel 20. Needle 12 and cartridge 30 are then inserted into the rear end of cartridge holder 50. Needle 12 is pushed to the front end of cartridge holder 50 and barrel 20 so that the needle cover 13 of the needle projects through the front end of the barrel, and hub flange 19 abuts against the front interior wall of the cartridge holder. Advancer 70 is then positioned at the rear end of cartridge holder 50 such that bosses 76 on advancer shaft 74 are aligned with the keyways 73 in the cartridge holder. Once the bosses 76 are aligned with keyways 73, advancer 70 is pushed into the rear end of cartridge holder 50 until the bosses contact the rear ends of helical channels 78. Advancer hub 72 is then rotated to push cartridge 30 forwardly into needle 12. The rear tip 16 of needle 12 ruptures the septum 36 at the forward end of cartridge 30 to connect the needle in fluid communication with the cartridge, as shown in FIG. 3.

Once the cartridge 30 is loaded into the barrel 20, plunger 40 is connected to the cartridge. Plunger rod 42 is inserted into the rear end of advancer 70 and through advancer bore 75. Since advancer bore 75 is coaxial with cartridge 30, the bore maintains the plunger rod 42 and plunger bore 43 in axial alignment with the threaded projection 37 on plug 38. Plunger 40 is screwed onto the plug 38 by axially rotating the plunger relative to the cartridge 30. The needle cover 13 is then removed from needle 12 to prepare the device for an injection.

Slight axial pressure is applied to the finger pad 44 of plunger 40 to purge any air from the cartridge 30 and/or needle 12. Once air is removed, the forward tip 14 of needle 12 is inserted into a patient. At this time, the plunger 40 may be pulled back and aspirated as necessary to verify that a blood vessel is pierced. The transparent or translucent sidewalls of barrel 20 and cartridge holder 30 allow the user to observe flashing of blood into the device 10. Axial pressure is then applied to finger pad 44 to advance the plunger rod 42 and cartridge plug 38 into the cartridge to expel medication through needle 12 and into the patient.

Plunger 40 is advanced forwardly into cartridge 30 until the forward end of plug 38 contacts the cartridge neck 31, as shown in FIG. 4. When plug 38 contacts the neck 31 in cartridge 30, plunger 40 is no longer axially displaceable forwardly in the cartridge, and the injection stroke is completed. Near the end of the injection stroke, plunger collar 46 contacts the tapered edges 29 of latches 27. Collar 46 displaces latches 27 out of engagement with flange 54 on cartridge holder 50. With the needle retainer arms 26 disengaged from flange 54, needle 12 is no longer maintained in the extended position against the bias of spring 24 by the retainer arms. Instead, needle 12 is maintained in the extended position against the bias of spring 24 by the axial pressure applied to finger pad 44.

The needle is retracted into the barrel 20 by releasing axial pressure on finger pad 44. Once axial pressure on finger pad 44 is released, no force is present to counteract the bias of spring 24. The spring 24 therefore expands, propelling cartridge holder 50 rearwardly relative to barrel 20. As discussed earlier, the forward end of cartridge holder 50 engages the flange 19 on needle hub 18 and forward end of cartridge 30. Therefore, needle hub 18, needle 12, cartridge 30 are pulled rearwardly as the cartridge holder 50 is displaced by spring 24. The forward tip 14 of needle 12 is propelled to the retracted position where it is enclosed within the barrel.

During needle retraction, the outwardly deflected retaining arms 26 ride along the exterior of plunger collar 46 as the plunger 40 is displaced rearwardly relative to the barrel 20. The forward end of plunger collar 46 remains in contact with the rear edge of flange 54 on cartridge holder 50 during retraction. When the forward edge of plunger collar 46 is retracted past latches 27, the latches remain outwardly deflected and ride over flange 54, allowing the flange to be retracted past the latches. Once flange 54 clears the latches, the resilient retaining arms 26 snap inwardly so that the latches protrude once again into the barrel 20. Lockout arms 56 and ribs 57 on cartridge holder 50 slidably engage longitudinal grooves 60 and slots 62 in barrel 20 to impede rotation of the cartridge holder during retraction.

As discussed earlier, the outward edges of lockout arms 56 and lockout tabs 58 are biased against the interior wall of barrel 20 due the resilient properties of the lockout arms. Cartridge holder 50 is propelled rearwardly until lockout tabs 58 align with lockout windows 23. As tabs 58 align with windows 23, the resilient lockout arms 56 expand outwardly and protrude through the lockout windows, as shown in FIG. 5. Lockout tabs 58 engage with windows 23 to prevent axial displacement of cartridge holder 50. That is, the cartridge holder 50 and contaminated needle cannot be removed from barrel 20 by pulling back on the plunger 40. The entire device 10 may be disposed of into a sharps container or, alternatively, the plunger 40 may be unscrewed, cleaned and re-used with another injector if desired.

Referring now to FIGS. 7–10, a second embodiment 110 of the present invention is shown. Device 110 generally operates in the same manner as the first embodiment but features a different locking mechanism. The device 110 includes a longitudinal barrel 120 and a needle 112 extending from the barrel in fluid connection with a cartridge 130. A cartridge holder 150 is disposed around cartridge 130 and slidably engages the interior of barrel 120. A rearwardly biased compression spring 124 is disposed in the forward end of barrel 120 and is operable to propel the needle 112 and cartridge holder 150 rearwardly within the barrel. Needle 112 is maintained in an extended position by a pair of retaining arms 126 at the rearward end of barrel 120. Retaining arms 126 engage cartridge holder 150 to maintain needle 112 forwardly against the rearward bias of spring 124.

Figure 7:
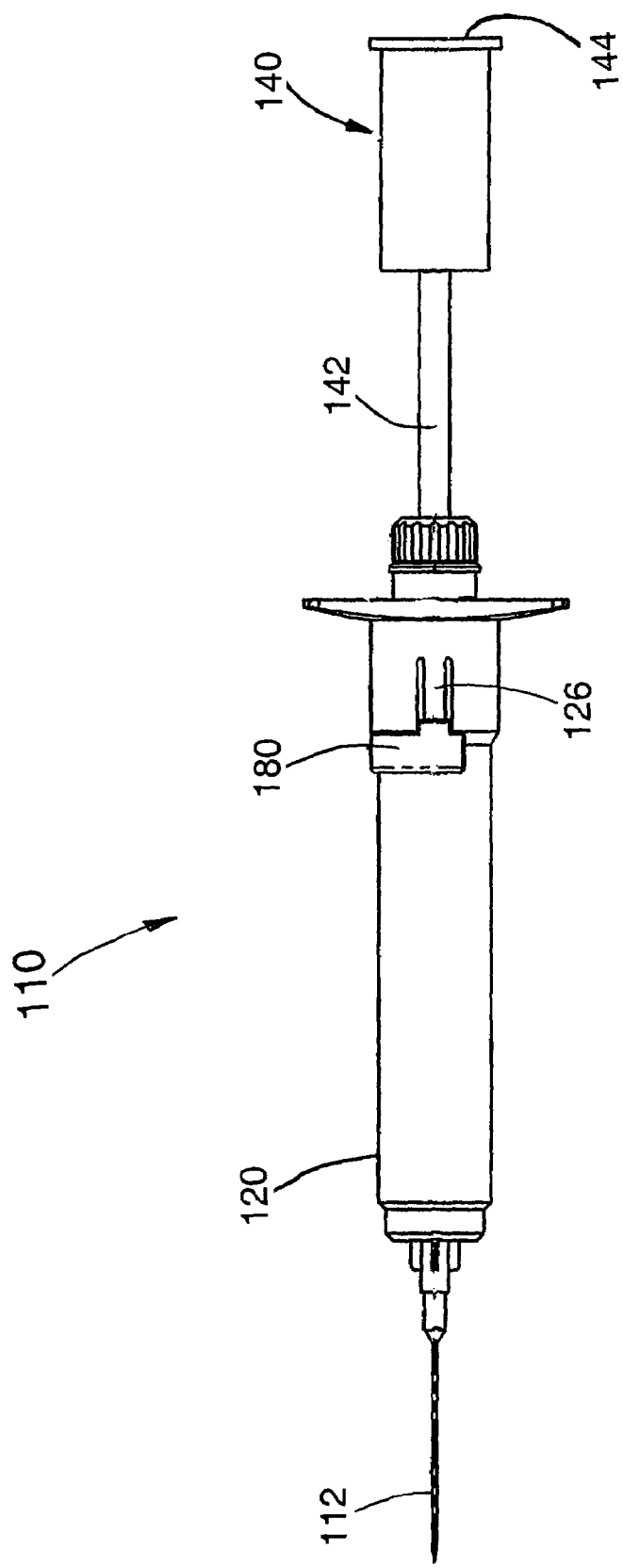
FIG. 7 is a perspective view of a second embodiment of a safety cartridge injection device.

After needle retraction, axial displacement of needle 112 is substantially prevented by a C-shaped locking clip 180 disposed around the barrel 120. Referring to FIG. 7, barrel 120 has a pair of opposed slots 123 that extend through the barrel wall near the rearward end of the barrel. Locking clip 180 is formed of a resilient flexible plastic material and is configured to lock around the barrel 120. Prior to attachment to the barrel, the free ends of locking clip 180 are deflected away from each other to allow the clip to fit around the exterior of barrel 120. Locking clip 180 has an interior face 182 and a pair of opposed tabs 184 extending inwardly from the interior face. Tabs 184 are configured to align with slots 123 on barrel 120 and protrude through the slots when locking clip 180 is attached to the barrel.

Figure 8:
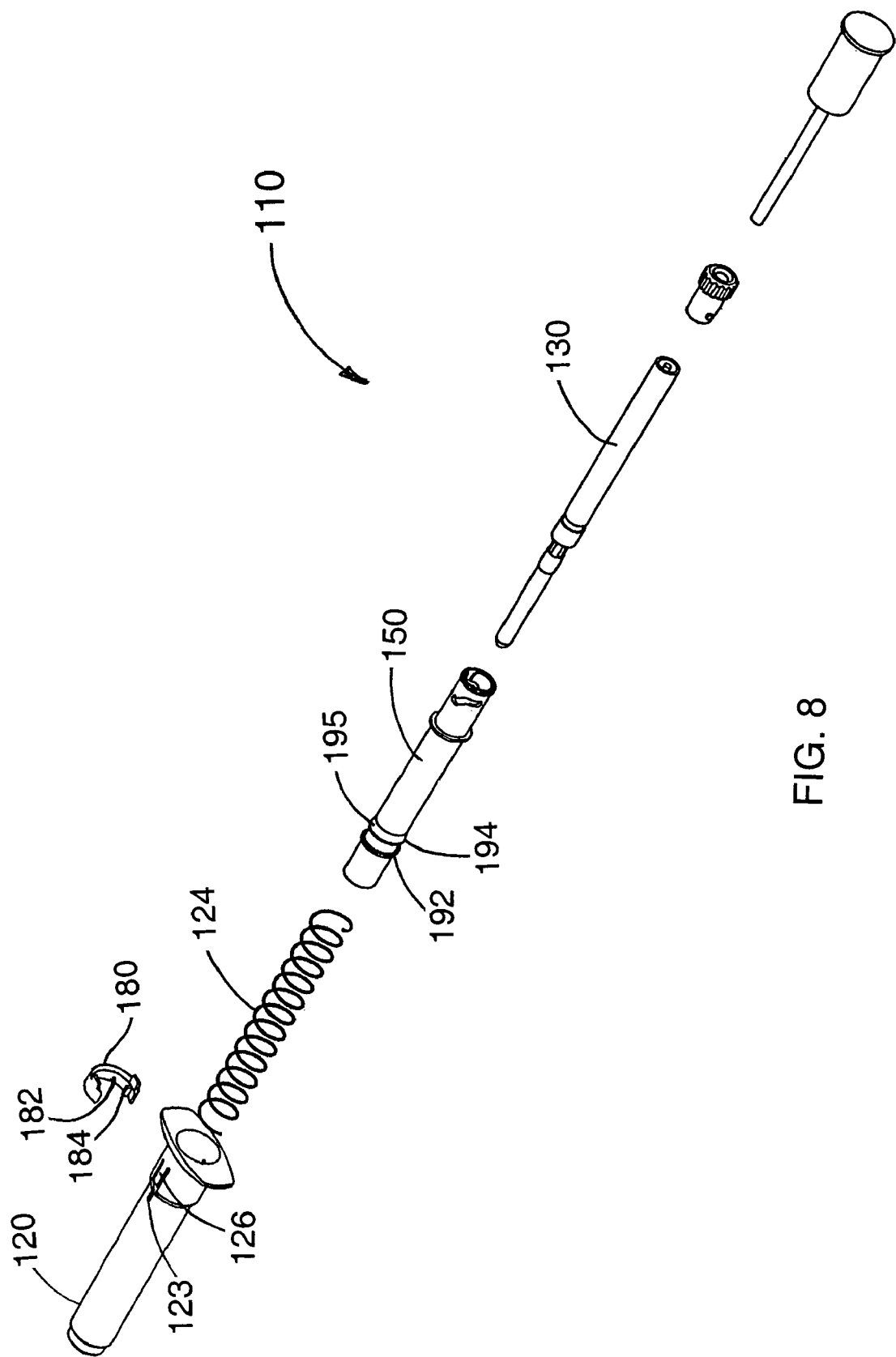
FIG. 8 is an exploded side elevational view of the device shown in FIG. 7.
Figure 9:
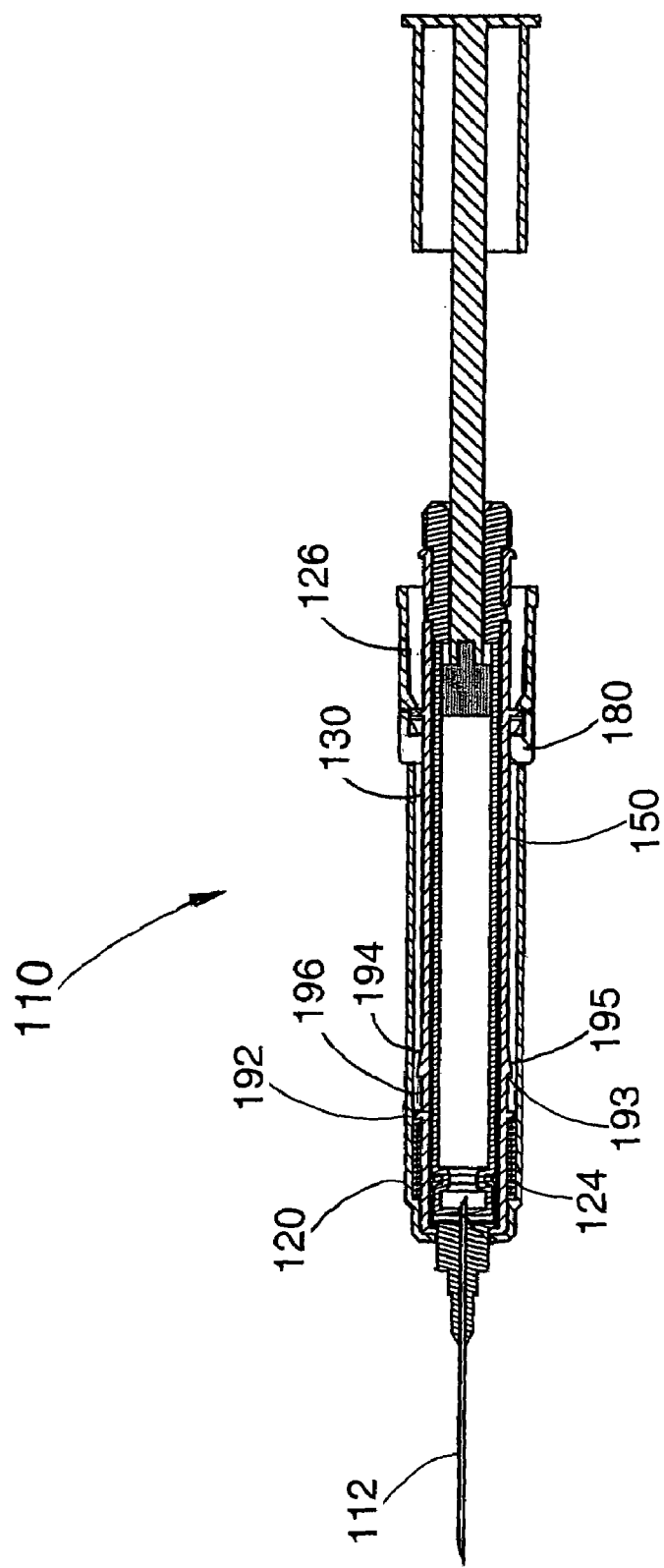
FIG. 9 is a cross-sectional view of the device shown in FIG. 7, illustrating the device prepared for an injection.

Referring now to FIGS. 8 and 9, a pair of circumferential flanges extend around the exterior of cartridge holder 150 near the forward end of the cartridge holder. In particular, cartridge holder 150 includes a first circumferential flange 192 having a forward edge that is generally normal to the needle retainer wall. First flange 192 is positioned in proximity to the forward end of cartridge holder 150 such that compression spring 124 bears against the first flange when needle 112 is retained in the extended position. A second circumferential flange 194 is disposed rearwardly from first flange 192. The second flange 194 has a forward face 193 that is substantially normal to the cartridge holder wall and a rearward face 195 that is tapered, as shown in FIG. 9. Second flange 194 is separated from first flange 192 forming a circumferential groove 196.

Flanges 192,194 are configured to cooperate with locking clip 180 to lock needle 112 inside the barrel 120 after an injection. In particular, tabs 184 on locking clip 180 are configured to engage first and second flanges 192,194 during needle retraction and snap into the annular recess 196 at the end of needle retraction. As cartridge holder 150 is propelled rearwardly by spring 124, tabs 184 contact the rear face 195 of second flange 194. Rear face 195 is gradually tapered to form a smooth transition extending radially outwardly from cartridge holder 150. As tapered rear face 195 of second flange 194 contacts the forward edges of tabs 184 during retraction, the tabs ride along the ramp-like face 195 and deflect radially outwardly. Tabs 184 slidably engage tapered face 195 to allow the second flange to pass rearwardly past the tabs.

Figure 10:
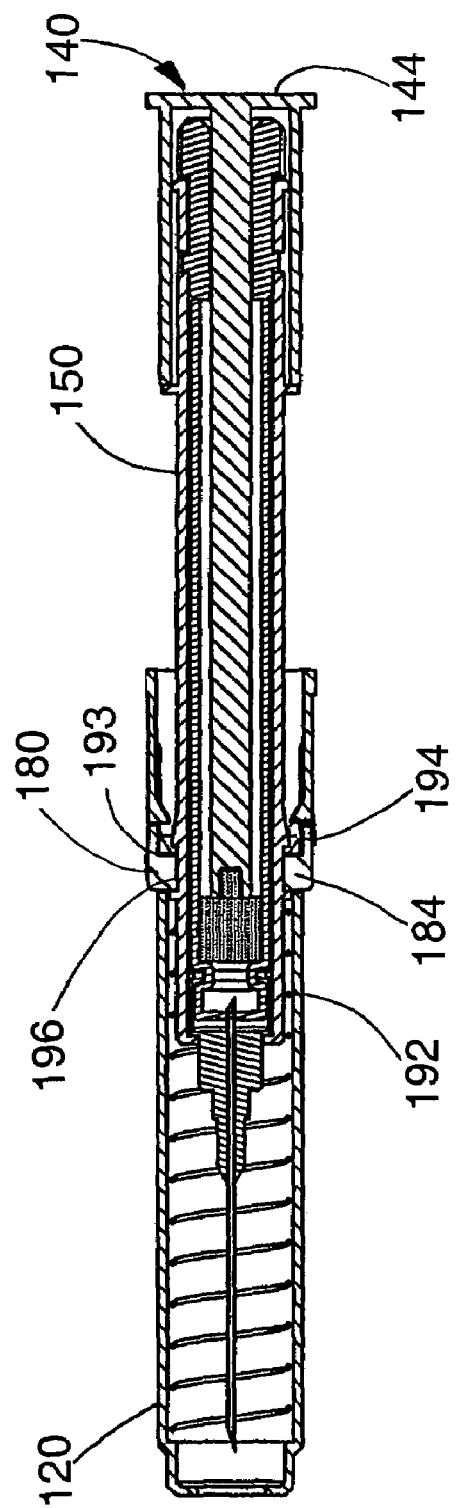
FIG. 10 is a cross-sectional view of the device shown in FIG. 7, illustrating the device after retraction of the needle.
Figure 11:
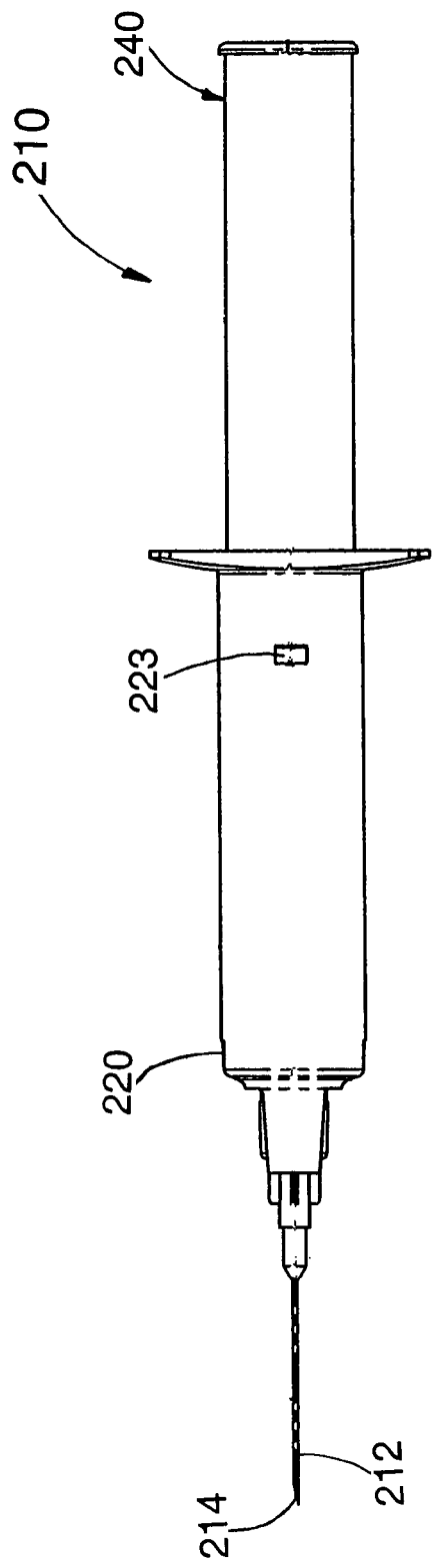
FIG. 11 is a perspective view of a third embodiment of a safety cartridge injection device.

The forward face 193 on second flange 195 is normal to the longitudinal axis of cartridge holder 150 and forms an abrupt transition into recess 196. After tabs 184 pass over the second flange 194, the tabs pass over forward face 193 and snap inwardly into recess 196, as shown in FIG. 10. Preferably, the longitudinal width of recess 196 is slightly greater than the longitudinal width of tabs 184 so that the tabs snap easily into the recess. Once tabs 184 are disposed in recess 196, further axial displacement of needle retainer 150 is substantially prevented. In particular, the normal rearward face of first flange 192 abuts the forward edges of tabs 184 to impede rearward displacement of needle retainer 150 relative to barrel 120. The normal forward face 193 on second flange 194 abuts the rearward edges of tabs 184 to impede forward displacement of needle retainer 150 relative to barrel 120.

Locking clip 180 offers advantages in the design and manufacturing of the invention. In particular, there is no need to limit rotation of needle retainer 150, because circumferential flanges 192,194 can engage the tabs 184 on locking clip 180, regardless of how the cartridge holder is rotated.

Figure 12:
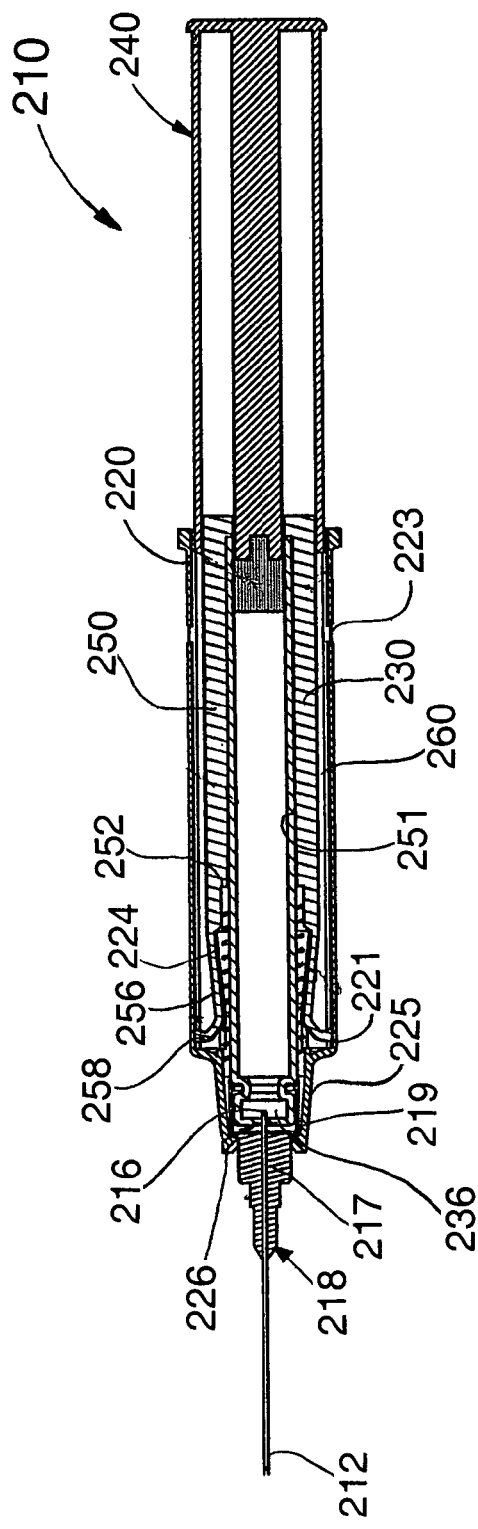
FIG. 12 is a first cross-sectional view of the device shown in FIG. 11, illustrating the device prepared for an injection.

Referring now to FIGS. 11–14, a third embodiment 210 of the present invention is illustrated. Device 210 generally operates similarly to the previous embodiments but includes fewer components. The device 210 includes a cylindrical barrel 220 containing a cartridge 230 pre-filled with a medication and a plunger 240 connected to the rearward end of the cartridge. A double-ended needle 212 extends from the forward end of barrel 220 in fluid connection with cartridge 230. The plunger 240 is axially displaceable in the barrel 220 to expel medication from cartridge 230 during an injection. After completion of an injection, a compression spring 224 in the front end of barrel 220 automatically propels needle 212 into the barrel when pressure is released from the plunger. Unlike the previous embodiments, cartridge 230 is loaded into the device 210 through the front end of barrel 220. The front end of barrel 220 has an orifice 221 adapted to receive the rear end of cartridge 230, as shown in FIG. 12. The barrel 220 contains a cartridge holder 250 having an open front end that is coaxial with orifice 221. Cartridge holder 250 includes an interior bore 251 that houses rear end of spring 224. Four longitudinal ribs 252 extend radially inwardly in the rear end of bore 251. The front edges of ribs 252 are co-planar and are normal to the longitudinal axis of barrel 220. The rear end of spring 224 bears against front edges of ribs 252 to bias cartridge holder 250 toward the rear end of the device 210.

Referring now to FIG. 12, a pair of resilient cantilever arms 225 extend forwardly from orifice 221 on barrel 220 and converge radially inwardly in a contracted position. As in previous embodiments, needle 212 extends through a generally cylindrical needle hub 218 having a base 217 and an outwardly extending flange 219 at the rear end of the hub. The cantilever arms 225 are configured to engage needle hub 218 to secure the needle to the device. In particular, each arm 225 has a radially inwardly extending latch 226 at the end of the arm that is configured to snap over the needle hub to secure the needle hub to the barrel.

Cantilever arms 225 are formed of a resilient flexible plastic that allow the arms to be deflected radially outwardly from the contracted position to an expanded position. In the expanded position, the opening between arms 225 is sufficient to allow insertion of the cartridge 230 and needle hub 218 into the barrel 220. Preferably, latches 226 are rounded or tapered so that cantilever arms 225 deflect outwardly as the rear end of cartridge 230 is inserted between the arms and into the barrel 220. When the cantilever arms 225 are deflected outwardly, the arms are biased inwardly due to the resilient property of the arms. After cartridge 230 and needle hub flange 219 pass latches 226, cantilever arms snap inwardly toward the contracted position, and latches 226 bear against the needle hub base. Latches 226 frictionally engage needle hub 218 to securely hold needle 212 to the barrel.

Device 210 is configured to inject a medication from a standard pre-filled cartridge 230 having a pierceable septum 236, similar to the previous embodiments. Needle 212 has a sharpened rear tip 216 that is configured to puncture the pierceable septum 236 on cartridge 230 to connect the needle in fluid communication with the cartridge. Preferably, the length of cartridge 230 is slightly less than the axial distance between the rear edge of latches 226 and rear wall of bore 251 in cartridge holder 250. In this way, needle 212 pierces septum 236 when hub flange 219 is pushed past the latches 226 on cantilever arms 225 to secure the needle hub to the device 210. More specifically, prior to use, the needle hub 218 is disposed forwardly (relative to FIG. 12) so that the rearward tip of the needle is forward of the septum 236. When the cartridge and needle are inserted into the cartridge holder 250, the flange at the rear wall of bore 251 operates as a stop impeding further insertion of the cartridge 230. However, pushing the needle hub 218 further inward snaps the needle hub further onto the cartridge so that the rearward tip of the needle pierces the septum 236. Septum 236 is formed of a self-sealing elastomeric material that frictionally engages the exterior of needle 212 after the needle pierces the septum.

As stated earlier, the rear end of spring 224 bears against the front edges of longitudinal ribs 252 to bias the cartridge holder 250 rearwardly. Spring 224 is operable to propel cartridge holder 250 rearwardly in the barrel during needle retraction. Ribs 252 are configured to form an interference fit with the exterior of cartridge 230. As such, ribs 252 frictionally engage the exterior of cartridge 230 so that when the cartridge holder is retracted, the cartridge and attached needle are retracted as well.

Referring now to FIG. 13, needle 212 is maintained in an extended position against the bias of spring 224 by a pair of resilient retaining arms 270 that extend radially outwardly from cartridge holder 250. Each retaining arm 270 has a retaining tab 272 extending outwardly from the forward end of the retaining arm. During assembly of device 210, retaining arms 270 are deflected radially inwardly and inserted in the rear end of barrel 220. When cartridge holder 250 is disposed in barrel 220, retaining arms 270 remain deflected inwardly so that the arms are biased outwardly against the interior wall of barrel 220. Prior to use of the device 210, retaining arms 270 are aligned with a pair of opposed retaining apertures 228 in the barrel wall near the front of the barrel. Retaining tabs 272 are configured to project through retaining apertures 228 and engage the side walls of the apertures to prevent axial displacement of cartridge holder 250 in response to the bias of the spring 224.

At the completion of an injection stroke, plunger 240 is operable to disengage needle retaining arms 270 and facilitate needle retraction. Plunger 240 has a finger pad 244 and a cylindrical sleeve 246 extending forwardly from the front edge of the finger pad into the barrel 220. The front edge of plunger sleeve 246 is aligned with the rear edges of needle retaining arms 270 so that the sleeve contacts the retaining arms during forward displacement of the plunger 240. As the front edge of sleeve 246 contacts the linear rear edges of retaining arms 270, the retaining arms are deflected radially inwardly, displacing the retaining tabs 272 out of engagement with retaining apertures 228. Once the tabs 272 are disengaged from apertures 228, needle 212 is no longer held against the bias of spring 224 by retaining arms 270. Instead, needle 212 is held against the bias of spring 224 by axial pressure supplied to finger pad 244. When pressure is released from finger pad 244, the spring operates to retract the needle retainer 250 and needle 212 rearwardly.

As with the first embodiment, a pair of resiliently flexible opposed lockout arms 256 extend forwardly and radially outwardly from cartridge holder 250, as shown in FIG. 12. The lockout arms 256 are molded to cartridge holder 250 and operate to limit displacement of the cartridge holder after retraction. Lockout arms 256 extend over the exterior of spring 224 and engage the interior wall of barrel 220. Each lockout arm 256 has a lockout tab 258 extending radially outwardly at the front end of the arm. Lockout tabs 258 slidably engage a pair of opposed grooves 260 that extend longitudinally in the interior wall of barrel 220. During retraction of needle 212, the sidewalls in grooves 260 engage the sides of lockout tabs 258 to minimize rotation of cartridge holder 250 in barrel 220. Lockout arms 256 extend generally parallel to the longitudinal axis of cartridge holder 250 prior to assembly of the device 210. During assembly of the device 210, lockout arms 256 are deflected radially inwardly toward one another so that lockout tabs 258 can enter the rear end of barrel 220. As a result, lockout arms 256 are biased radially outwardly and bear against the interior wall of barrel 220 once needle retainer 250 is disposed in the barrel. A pair of lockout windows 223 are disposed in the rear end of barrel 220 and extend through the barrel wall into grooves 260. The lockout windows 223 are adapted to receive and cooperate with lockout tabs 258 during needle retraction to limit axial displacement of the needle after needle retraction. In particular, lockout windows 223 are positioned such that lockout tabs 258 align with the windows during rearward displacement in grooves 260. Once aligned with windows 223, lockout tabs 258 snap outwardly into engagement with the windows, as shown in FIG. 14. Lockout tabs 258 are configured to extend outwardly through lockout windows 223 such that the sides of the tabs contact the sides of the windows to prevent further axial displacement of cartridge holder 250 after retraction of needle 212.

Referring now to FIGS. 15–21 a fourth embodiment of a safety pre-filled cartridge injector is designated generally 310. The device 310 operates similarly to the previous embodiments. A cartridge 330 and needle assembly are received in an inner housing 350 that operates as a cartridge holder. The cartridge holder 350 is axially displaceable within an outer barrel 320. A plunger 340 cooperates with the cartridge 330 to expel the medicine from the cartridge. The cartridge holder 350 and attached needle 312 are biased rearwardly by a spring 324. A locking clip 360 retains the cartridge holder 350 in a forward position during use, so that the needle projects forwardly from the barrel 320. After use, the locking clip 360 releases the cartridge holder 350, so that the spring 324 can retract the cartridge holder and attached needle 312.

Figure 15:
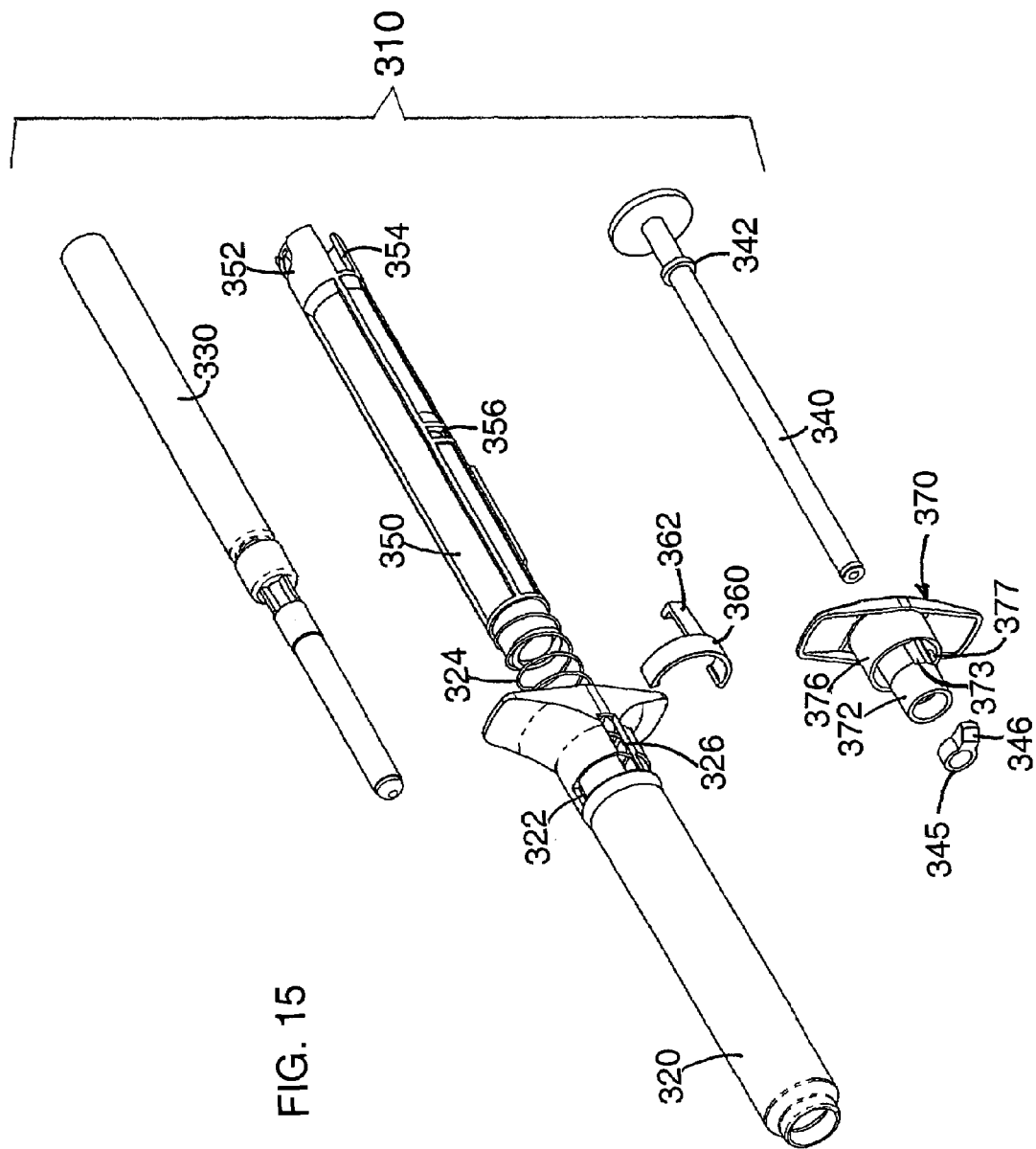
FIG. 15 is an exploded side elevational view of a fourth embodiment of a safety cartridge injection device.
Figure 16:
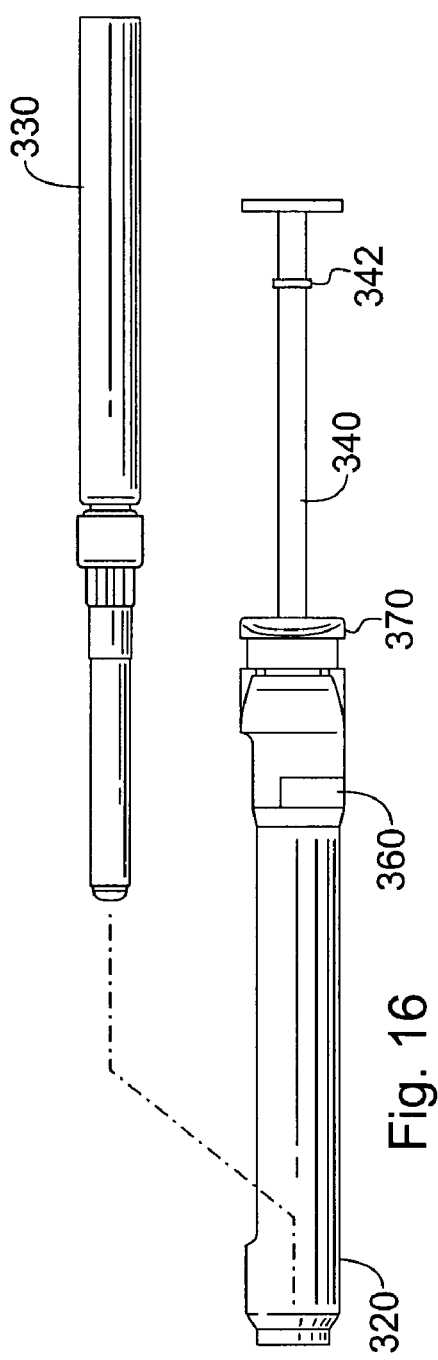
FIG. 16 is a side elevational view of the cartridge injector of FIG. 15 illustrating the injector separated from a cartridge/needle assembly.

Referring now to FIGS. 15 and 16, the details of the device 310 will be described in greater detail. The barrel 320 is a generally cylindrical element having an open rearward end and a forward end having a reduced diameter opening. A pair of finger flanges are formed on the rearward end of the barrel to provide a gripping surface for the medical professional during use. An elongated slot forms an access opening 328 in the side of the barrel (see FIGS. 16 and 21) so that the cartridge 330 and needle assembly can be inserted through the access opening rather than through the rearward end of the barrel.

Adjacent the rearward end of the barrel a recess is formed that is shaped to cooperate with the locking clip 360. Specifically, the recess includes a circumferential recess extending around approximately half of the circumference of the barrel, as shown in FIG. 15. A pair of windows 322 are formed in the barrel at the circumferential ends of the recess. As described further below, the windows 322 cooperate with the locking clip 360 to attach the locking clip to the barrel 320. In addition to the circumferential recess an axial recess intersects the circumferential recess. At the rearward end of the axial recess a locking aperture 326 is provided in the barrel 320. A portion of the locking clip 360 projects through the locking aperture 326 to releasably engage the cartridge holder 350, as described further below.

The locking clip 360 comprises a generally c-shaped clip having an integral axially elongated resilient latch 362. The circumferential ends of the c-clip form locking tabs that cooperate with the windows 322 in the barrel to attach the locking clip to the barrel. The latch 362 is radially deformable and projects radially inwardly through the locking aperture 326 in the barrel.

The cartridge 330 and needle assembly are preferably configured similarly to the Carpuject cartridge produced by Abbott Laboratories, Inc. Such a cartridge and needle assembly may be pre-assembled and packaged separately from the injection device 310. Specifically, the needle assembly comprises a double-ended needle 312 fixedly attached to a needle hub 318. The rearward end of the needle hub 318 forms a socket having an annular ridge projecting radially inwardly to cooperate with a pair of circumferential grooves on the cartridge. In this way, the needle hub 318 is snap-fit onto the cartridge 330.

Figure 17:
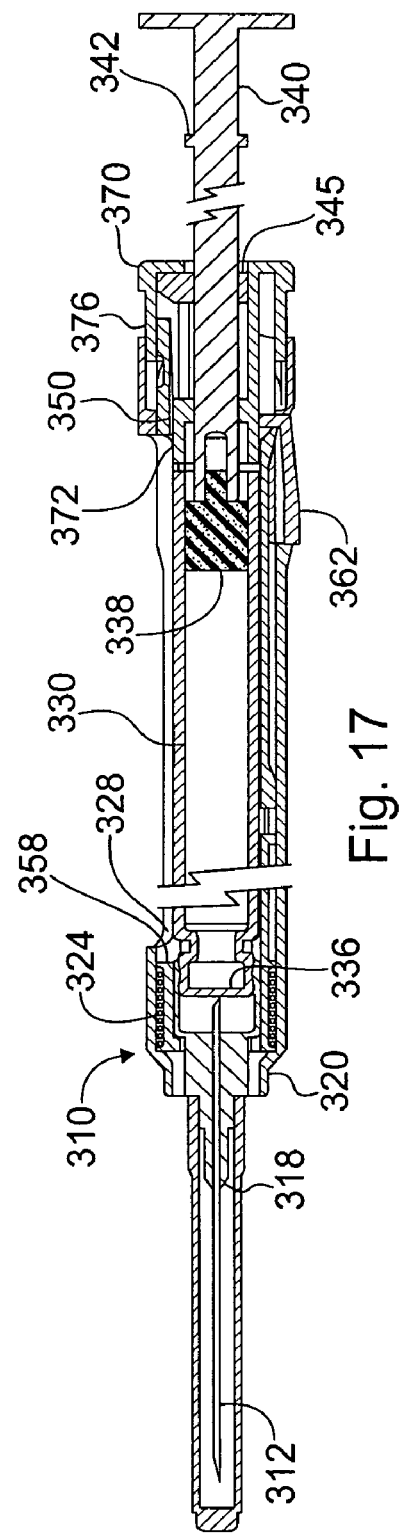
FIG. 17 is a cross-sectional view of the device illustrated in FIG. 15.

The cartridge 330 is preferably a pre-measured dose of a medicinal fluid. The cartridge comprises a fluid container having a open rearward end that is sealed by a piston 338, and a forward end that is sealed by a pierceable septum 326. A pair of axially spaced circumferential grooves formed on the exterior surface of the forward end of the cartridge cooperate with the needle hub 318 to attach the needle to the cartridge. The forward groove cooperates with the needle hub 318 to attach the needle to the cartridge in a first position as shown in FIG. 17. In this position, the needle 312 is held forward of the septum 326 so that the needle does not pierce the septum, thereby preventing leakage prior to use. Referring to FIG. 18, by advancing the cartridge relative to the needle hub 318, the rearward end of the needle 312 pierces the septum 326 so that the needle is in fluid communication with the interior of the cartridge. In this second position, the needle hub 318 cooperates with the rearward circumferential groove on the cartridge to attach the needle to the cartridge.

The cartridge holder 350 is configured to receive the cartridge 330 and attached needle 312. The cartridge holder 350 is a generally hollow cylinder having open ends. An access opening 358 is formed in the sidewall of the holder to allow the cartridge 330 and needle assembly to be inserted into the holder through the side of the device, as shown in FIG. 16. The access opening 358 is similar to, and circumferentially aligned with the access opening 328 in the barrel, as shown in FIG. 17.

The forward end of the cartridge holder 350 has a reduced exterior diameter. The rearward edge of the reduced exterior surface forms a circumferential flange against which the spring 324 bears to bias the holder rearwardly. In addition, the open forward end of the holder has an annular lip projecting radially inwardly so that the forward open end has a smaller diameter than the diameter of the needle hub 318. In this way, the annular lip operates as a stop, preventing the needle assembly and cartridge 330 from passing through the forward open end of the holder.

A lockout window 356 is formed in the side of the cartridge holder 350 intermediate the forward and rearward ends of the holder. The lockout window 356 is cooperable with the locking clip 360 to lock the holder in a retracted position, as discussed further below. A holder slot 354 formed in the side of the holder is axially aligned with the lockout window 356. The holder slot 354 is formed at the rearward end of the holder 350 and extends to the rearward edge of the holder so that the slot is open at the rearward edge, as shown in FIG. 15.

A helical groove 352 is formed on the exterior surface of the cartridge holder 350, circumferentially spaced from the holder slot 354. The helical groove 352 extends approximately 180 degrees around the circumference of the holder. As shown in FIG. 15, the rearward end of the groove forms an axial recess that terminates at the rearward end of the holder. The axial recess allows the adapter 370 to snap fit into the groove, as discussed further below.

The advancer 370 is attached to the rearward end of the cartridge holder 350, and is operable to advance the cartridge 330 prior to use so that the rearward tip of the needle 312 pierces the septum 336 of the cartridge. The advancer comprises an elongated inner cylinder 372 and a coaxial outer cylinder 376. The inner cylinder has a diameter that is substantially similar to the diameter of the cartridge 330 so that the inner cylinder can be inserted into the rearward end of the cartridge holder 350. The forward rim of the inner cylinder 372 is operable to engage the cartridge 330 to advance the cartridge. Referring to FIG. 15, an advancer slot 373 is formed in the sidewall of the inner cylinder 372. The advancer slot 373 is sized to cooperate with a trigger 345, as discussed further below.

The outer cylinder 376 of the advancer 370 has a diameter that is greater then the external diameter of the cartridge holder 350 and smaller than the interior diameter of the rearward end of the barrel 320. Referring to FIGS. 15 and 19, a drive pin 377 projects radially inwardly from the forward edge of the outer cylinder 376. The drive pin 377 forms a snap fit with the helical groove 352 on the cartridge holder to attach the advancer 370 to the cartridge holder. The drive pin is configured so that it can slide within the helical groove 352.

An annular flange projects radially inwardly from the inner cylinder 372, spaced rearwardly from the front edge of the inner cylinder. The annular flange provides a reduced diameter opening that is sized to correspond to the diameter of the plunger 340. Specifically, the reduced diameter opening provided by the annular flange in the inner cylinder 372 is slightly larger than the diameter of the plunger rod to provide a sliding fit between the plunger 340 and the inner cylinder. Additionally, the reduced diameter opening in the inner cylinder is preferably co-axial with the cartridge 330 so that the reduced diameter opening in the inner cylinder operates as a guide to align the plunger rod with the piston 338 in the cartridge. In this way, the plunger 340 can be readily attached to the piston 338.

Referring to FIGS. 15 and 17, the details of the plunger 340 can be seen most clearly. The plunger 340 is an axially elongated cylindrical rod having a connector at the front end configured to mate with the piston 338 in the cartridge 330. For instance, the plunger may have a barb to attach the plunger to the piston 338. However, in the present instance, the plunger is illustrated as having an internally threaded socket that mates with a threaded stem on the piston 338 to threadedly connect the plunger to the cartridge. The plunger 340 has a circumferential actuation flange 342 that projects radially outwardly, adjacent the rearward end of the plunger. The actuation flange 342 has a diameter that is smaller than the internal diameter of the inner cylinder 372. In this way, the actuation flange 342 can be inserted into the inner cylinder 372. As discussed further below, the actuation flange cooperates with the trigger 345 to actuate retraction of the needle 312.

Referring to FIG. 15, the trigger 345 has a ring-shaped body portion and a radially projecting protrusion 346 that operates as an actuation surface. The trigger has an aperture sized to cooperate with the plunger 340, so that plunger rod can slide through the trigger. The outer diameter of the ring-shaped portion of the trigger 345 is smaller than the internal diameter of the inner cylinder 372 of the advancer 370. However, the outer diameter of the trigger 345 including the protrusion 346 is greater than the internal diameter of the inner cylinder. As shown in FIG. 17, the protrusion 346 projects into the slot 373 in the inner cylinder 372. In addition, the width of the protrusion 346 is less than the width of the slot 373, so that the trigger can be displaced axially within the advancer. The front face of the trigger protrusion 346 is tapered to provide an angled actuation surface to displace the locking clip latch 362 radially outwardly, as discussed further below.

Preferably, the device 310 is configured so that the injector can be shipped as an assembled unit with the cartridge 330 and needle assembly provided as a separate sub assembly. The cartridge 330 and needle assembly are then inserted into the cartridge holder 350 through the access openings 328, 358 in the cartridge holder and the barrel 320. The plunger 340 is then attached to the piston 338 in the cartridge and the advancer 370 moves the cartridge forward so that the needle 312 pierces the septum 336 of the cartridge. The plunger 340 is displaced axially forwardly to drive the piston 338 forwardly in the cartridge to inject medicine into a patient. At the end of the injection stroke the plunger 340 engages the trigger 345 and displaces the trigger forwardly so that the trigger displaces the latch 362 on the locking clip 360 radially outwardly to actuate retraction. The spring 324 then displaces the cartridge holder 350 rearwardly along with the needle 312 and the plunger 340. After the needle is retracted, the device 310 can be safely disposed.

The operation of the device will now be described in greater detail. The injector is assembled by inserting the spring 324 into the forward end of the barrel 320 so that the forward end of the spring bears against the forward end of the barrel. The cartridge holder 350 is then inserted into the rearward end of the barrel 320 and advanced toward the forward end of the barrel, thereby compressing the spring 324. The locking clip 360 is then attached to the barrel so that the latch 362 projects into the barrel, engaging the forward end of the slot 354 to retain the cartridge holder against the bias of the compressed spring 324.

The trigger 345 is inserted into the advancer 370 through the slot 373 in the inner cylinder 372 so that the protrusion 346 on the trigger projects into the slot in the inner cylinder. The plunger 340 is then inserted into the advancer 370 so that the plunger rod passes through the trigger 345 and the internal flange in the inner cylinder 372. Preferably, a circumferential rib is formed on the exterior surface of the forward end of the plunger, so that the plunger is press fit through the internal flange in the inner cylinder during assembly, and the circumferential rib cooperates with the internal flange to impede removal of the plunger from the advancer. The advancer 370 with the attached plunger 340 and trigger 345 are then snap fit to the cartridge holder 350 by inserting the drive pin 377 into the helical groove 352 at the rearward end of the holder. Once the advancer is attached to the inner housing, the injector assembly is complete.

To use the injector, a cartridge/needle assembly is inserted into the cartridge holder 350. To ensure that the plunger 340 does not interfere with insertion of the cartridge/needle assembly, the plunger is withdrawn so that the forward end of the plunger does not project beyond the forward end of the advancer 370. By providing the access openings 328, 358 in the side of the barrel and cartridge holder, the advancer 370 and plunger 340 need not be removed to insert the cartridge/needle assembly. Instead, the cartridge/needle assembly are inserted into the cartridge holder through the access openings 328, 358, and are slid forwardly until the needle hub 318 abuts the interior flange at the front end of the cartridge holder. The plunger 340 is then advanced to engage the piston 338 in the cartridge 330. In the present instance, the plunger 340 is then rotated to screw the plunger onto the piston 338. At this point, the device 310 is configured as illustrated in FIG. 17. The detents of the needle hub 318 cooperate with the forward circumferential groove on the head of the cartridge 330 to hold the cartridge away from the needle 312 so that the needle does not pierce the septum 336.

To prepare the injector for use, the advancer 370 is rotated clockwise approximately 180 degrees. The drive pin 377 on the advancer 370 follows the helical groove 352 on the holder 350, which drives the advancer 370 axially forwardly to the position shown in FIG. 18. In turn, the inner cylinder 372 of the advancer 370 engages the cartridge 330, driving the cartridge forward. Since the needle hub 318 abuts the forward end of the cartridge holder 350, when the cartridge is driven forwardly, the cartridge is driven further into the needle hub so that the rearward end of the needle 312 pierces the septum of the cartridge.

After the advancer 370 is twisted to drive the cartridge forward, the advancer slot 373 is aligned with an axially extending groove formed in the interior of the barrel 320 at the rearward end of the barrel. The protrusion 346 on the trigger 345 projects through the advancer slot 373 and the groove in interior of the barrel 320 thereby preventing rotational displacement of the cartridge holder relative to the barrel.

The medical professional then drives the plunger 340 forwardly, which in turn drives the piston 338 forwardly through the cartridge 330. Since the piston 338 forms a fluid-tight seal with the interior of the cartridge, the piston expels the medicinal fluid from the cartridge as it is advanced through the cartridge. As the plunger 340 is advanced, the actuation flange 342 engages the trigger 345 and drives the trigger forwardly. At the end of the injection stroke, the actuation flange 342 drives the trigger 345 into the latch 362 on the locking clip 360. Specifically, the tapered face of the protrusion 346 on the trigger 345 is driven into the latch 362. The latch 362 rides up the tapered face of the protrusion so that the trigger 345 displaces the latch radially outwardly, as shown in FIGS. 20 and 20A. After the latch 362 is displaced out of engagement with the cartridge holder 350, the only force holding the cartridge holder against the bias of the spring 324 is the force supplied by the medical professional pushing against the back of the plunger 340. Accordingly, when the medical professional releases the plunger, the spring 324 displaces the cartridge holder 350 rearwardly along with the needle assembly, so that the forward sharpened tip of the needle is enclosed within the barrel.

As the cartridge holder is retracted, the latch 362 rides along the exterior of the cartridge holder until the lockout window 356 is aligned with the latch 362. The latch 362 then projects into the lockout window 356 in the cartridge holder to lock the cartridge holder and the attached needle in the retracted position, as shown in FIG. 21.

As can be seen from the foregoing, the device 310 provides a safety injector that can readily accommodate existing cartridge/needle assemblies. To use the device, the medical professional simply needs to insert the cartridge/needle assembly into the injector, attach the plunger to the piston and then the twist the advancer 180 degrees so that the device is ready for injection. The injection is then given in the same manner as is currently used with non-safety devices. At the end of the injection retraction is automatically actuated so that the needle is retracted as soon as the medical professional releases pressure on the plunger.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention. Accordingly, the invention incorporates variations that fall within the scope of the following claims.

We claim:

1. A medical device comprising:
   a hollow barrel having a forward end;
   a cartridge disposed within the barrel containing a medication;
   a needle having a sharpened forward end and operable between an extended position, in which the sharpened forward end projects from the forward end of the barrel, and a retracted position, in which the sharpened forward end is enclosed within the barrel;
   a plunger slidably disposed in the cartridge and operable to expel the medication from the cartridge;
   a biasing element that biases the needle towards the retracted position; and
   a needle retainer releasably engaging the barrel to maintain the needle in the projecting position against the force of the biasing element,
   wherein axial pressure on the plunger displaces the plunger forwardly to expel medication from the cartridge and release the needle retainer from engagement with the barrel, after which the needle is automatically propelled from the extended position to the retracted position by releasing pressure on the plunger.

2. The medical device of claim 1 comprising a cartridge holder disposed around the needle and cartridge, said cartridge holder comprising a radially outwardly extending detent.

3. The medical device of claim 2, wherein the needle retainer comprises:
   a resilient flexible arm attached to the barrel; and
   an inwardly extending tab on the flexible arm configured to engage the detent on the cartridge holder when the needle tip is in the extended position.

4. The medical device of claim 3, wherein the plunger comprises a cylindrical sleeve having a forward end configured to displace the inwardly extending tab out of engagement with the detent as the plunger is advanced forwardly into the barrel.

5. The medical device of claim 1 comprising a lock on the cartridge holder that substantially limits displacement of the needle after the needle is in the retracted position.

6. The medical device of claim 5 wherein the lock comprises a resilient flexible arm extending radially outwardly form the cartridge holder and configured to engage a window at the rearward end of the barrel when the needle is displaced to the retracted position.

7. The medical device of claim 1 wherein the cartridge comprises a piston having a threaded projection configured to mate with a threaded recess on the forward end of the plunger.

8. A medical device comprising:
   a cartridge containing a medication;
   a hollow barrel having a forward end adapted to receive the cartridge into the barrel;
   a needle having a sharpened forward end and operable between an extended position, in which the sharpened forward end projects from the forward end of the barrel, and a retracted position, in which the sharpened forward end is enclosed within the barrel;
   a plunger slidably disposed in the cartridge and operable to expel the medication from the cartridge;
   a biasing element that biases the needle towards the retracted position; and
   a needle retainer releasably engaging the barrel to maintain the needle in the projecting position against the force of the biasing element;
   wherein axial pressure on the plunger displaces the plunger forwardly to expel medication from the cartridge and release the needle retainer from engagement with the barrel, after which the needle is automatically propelled from the extended position to the retracted position by releasing pressure on the plunger.

9. The medical device of claim 8 comprising a cartridge holder disposed around the needle and cartridge.

10. The medical device of claim 9 comprising an aperture in the barrel wall near the forward end of the barrel.

11. The medical device of claim 10, wherein the needle retainer comprises a resilient flexible arm extending radially outwardly from the cartridge holder and configured to releasably engage the aperture in the barrel wall when the needle is in the extended position.

12. The medical device of claim 11, wherein the plunger comprises a cylindrical sleeve having a forward end configured to displace the resilient flexible arm out of engagement with the aperture in the barrel wall as the plunger is advanced forwardly into the barrel.

13. The medical device of claim 8 comprising a lock on the cartridge holder that substantially limits displacement of the needle after the needle is in the retracted position.

14. The medical device of claim 13 wherein the lock comprises a resilient flexible arm extending radially outwardly form the cartridge holder and configured to engage a window at the rearward end of the barrel when the needle is displaced to the retracted position.

15. The medical device of claim 8 wherein the cartridge comprises a piston having a threaded projection configured to mate with a threaded recess on the forward end of the plunger.

16. A medical device for injecting medicinal fluid from a cartridge assembly comprising a cartridge having a quantity of medicinal fluid sealed by a septum, and a needle having a sharpened tip attached to the cartridge, comprising:
   a hollow barrel;
   a cartridge holder configured to receive the cartridge assembly;
   a biasing element biasing the cartridge holder rearwardly;
   a retainer releasably retaining the cartridge holder in a forward position against the bias of the biasing element so that the needle is exposed for use;
   an advancer operable to drive the cartridge forward in the cartridge holder relative to the needle so that the needle pierces the septum;
   a plunger operable to expel the medicinal fluid from the cartridge;
   an actuator operable to release the retainer upon operation of the plunger;
   wherein at the end of an injection the actuator operates to release the retainer so that the biasing element displaces the cartridge holder rearwardly along with the cartridge assembly.

17. The medical device of claim 16 comprises a lock operable to lock the cartridge holder in a retracted position.

18. The medical device of claim 16 wherein the advancer is rotatable relative to the cartridge holder to advance to cartridge.

19. The medical device of claim 16 comprising an elongated slot formed in the side of the cartridge holder to provide an access opening so that the cartridge assembly can be inserted into the cartridge holder while the plunger is attached to the cartridge holder.

20. The medical device of claim 16 wherein the retainer is a radially deformable latch.

21. The medical device of claim 16 wherein actuator is longitudinally displaceable relative to the plunger.

22. The medical device of claim 16 wherein the plunger has an elongated rod and a circumferential flange projecting radially outwardly to engage the actuator.

23. The medical device of claim 22 wherein the flange is operable to drive the actuator axially forwardly to actuate retraction of the cartridge holder.

24. The medical device of claim 16 wherein the cartridge assembly comprising means for releasably retaining the needle spaced apart from the cartridge.

* * * * *